(12) United States Patent
Battlogg

(10) Patent No.: US 10,635,174 B2
(45) Date of Patent: Apr. 28, 2020

(54) HAPTIC INTERFACE WITH ROTARY ENCODER AND METHOD FOR ADJUSTING A SMART DEVICE

(71) Applicant: INVENTUS ENGINEERING GMBH, St. Anton im Montafon (AT)

(72) Inventor: Stefan Battlogg, St. Anton i.m. (AT)

(73) Assignee: INVENTUS Engineering GmbH, St.Anton im Montafon (AT)

( * ) Notice: Subject to any disclaimer, the term of this patent is extended or adjusted under 35 U.S.C. 154(b) by 12 days.

(21) Appl. No.: 15/397,204

(22) Filed: Jan. 3, 2017

(65) Prior Publication Data

US 2017/0115735 A1 Apr. 27, 2017

Related U.S. Application Data

(63) Continuation of application No. 14/747,025, filed on Jun. 23, 2015, which is a continuation-in-part of (Continued)

(30) Foreign Application Priority Data

Sep. 15, 2010 (DE) .......... 10 2010 045 436
Dec. 23, 2010 (DE) .......... 10 2010 055 833

(51) Int. Cl.
*G09G 5/00* (2006.01)
*G06F 3/01* (2006.01)
(Continued)

(52) U.S. Cl.
CPC ............ *G06F 3/016* (2013.01); *A61F 2/38* (2013.01); *A61F 2/60* (2013.01); *A61F 2/64* (2013.01);
(Continued)

(58) Field of Classification Search
CPC ...... G06F 3/016; G06F 3/0362; G06F 3/0482; G05G 1/08; G05G 5/03
(Continued)

(56) References Cited

U.S. PATENT DOCUMENTS 3,977,739 A 8/1976 Howe et al.
4,043,616 A 8/1977 Zimmer
(Continued)

FOREIGN PATENT DOCUMENTS

DE 1 927 328 A1 10/1970
DE 10 2004 009 906 B3 7/2005
(Continued)

*Primary Examiner* — Jennifer T Nguyen
(74) *Attorney, Agent, or Firm* — Laurence A. Greenberg; Werner H. Stemer; Ralph E. Locher

(57) ABSTRACT

A magnetorheological transmission device and a method for influencing the coupling intensity of two components, which can be coupled and whose coupling intensity can be influenced. To influence the coupling intensity, a channel is provided, which contains a magnetorheological medium with magnetically polarizable particles. A magnetic field generating unit generates a magnetic field in the channel in order to influence the magnetorheological medium in the channel. An outer component encloses an inner component. At least one of the two components is mounted via a separate bearing. A distance between the outer and inner components at least 10 times as great as a typical mean diameter of the magnetically polarizable particles in the magnetorheological medium. The magnetic field of the magnetic field generating unit can be applied to the channel in order to selectively chain together the particles and/or release them.

17 Claims, 11 Drawing Sheets

Related U.S. Application Data application No. 13/823,781, filed as application No. PCT/EP2011/004623 on Sep. 15, 2011, now Pat. No. 9,091,309.

(51) Int. Cl.

| | | |
|---|---|---|
| *F16D 37/02* | (2006.01) | |
| *F16D 57/00* | (2006.01) | |
| *G05G 5/03* | (2008.04) | |
| *A61F 2/38* | (2006.01) | |
| *A61F 2/60* | (2006.01) | |
| *A61F 2/64* | (2006.01) | |
| *A61F 2/66* | (2006.01) | |
| *G06F 3/0362* | (2013.01) | |
| G05G 1/08 | (2006.01) | |
| F16D 37/00 | (2006.01) | |
| A61F 2/50 | (2006.01) | |
| A61F 2/68 | (2006.01) | |
| G06F 3/0482 | (2013.01) | |

(52) U.S. Cl.
CPC ............ *A61F 2/6607* (2013.01); *F16D 37/02* (2013.01); *F16D 57/002* (2013.01); *G05G 5/03* (2013.01); *G06F 3/0362* (2013.01); *A61F 2002/5004* (2013.01); *A61F 2002/6836* (2013.01); *A61F 2002/6845* (2013.01); *A61F 2002/6863* (2013.01); *F16D 2037/002* (2013.01); *F16D 2300/0214* (2013.01); *F16D 2300/18* (2013.01); *G05G 1/08* (2013.01); *G06F 3/0482* (2013.01)

(58) Field of Classification Search
USPC .................................................. 345/156–184
See application file for complete search history.

(56) References Cited

U.S. PATENT DOCUMENTS

| | | | |
|---|---|---|---|
| 4,898,480 | A | 2/1990 | Raj et al. |
| 6,729,996 | B2 | 5/2004 | Green et al. |
| 2002/0057152 | A1* | 5/2002 | Elferich .................... H01F 7/08 335/220 |
| 2007/0063995 | A1* | 3/2007 | Bailey ................... G06F 3/0482 345/184 |
| 2007/0279401 | A1* | 12/2007 | Ramstein ................ G06F 3/016 345/184 |
| 2008/0053776 | A1 | 3/2008 | Moser et al. |
| 2010/0013761 | A1* | 1/2010 | Birnbaum ............... H04W 4/21 345/156 |
| 2011/0055120 | A1* | 3/2011 | Baskent ................. G06N 3/126 706/11 |

FOREIGN PATENT DOCUMENTS

| | | |
|---|---|---|
| DE | 10 2004 062 320 B4 | 7/2006 |
| DE | 10 2005 006 232 B3 | 11/2006 |
| DE | 10 2006 034 966 A1 | 1/2008 |
| DE | 10 2007 006 015 A1 | 8/2008 |
| DE | 10 2007 006 061 A1 | 8/2008 |
| DE | 10 2007 028 990 A1 | 12/2008 |
| DE | 10 2007 061 633 A1 | 6/2009 |
| EP | 1075979 B1 | 10/2005 |
| JP | 10176719 A | 6/1998 |
| WO | 2008/095460 A1 | 8/2008 |

\* cited by examiner

HAPTIC INTERFACE WITH ROTARY ENCODER AND METHOD FOR ADJUSTING A SMART DEVICE

CROSS-REFERENCE TO RELATED APPLICATION

This application is a continuation of copending application Ser. No. 14/747,025, filed Jun. 23, 2016, which was a continuation-in-part of copending patent application Ser. No. 13/823,781, now U.S. Pat. No. 9,091,309, issued Jul. 28, 2015, which was a § 371 national stage of international application PCT/EP2011/004623, filed Sep. 15, 2011; the application further claims the priority of German patent applications DE 10 2010 045 436, filed Sep. 15, 2010, and DE 10 2010 055 833, filed Dec. 23, 2010; the prior applications are herewith incorporated herein in their entirety.

BACKGROUND OF THE INVENTION

Field of the Invention

The present invention relates to a magnetorheological transmission device and in particular a magnetorheological force or torque transmission device, wherein the transmission between a first component and at least one second component, which is moving or resting relative thereto, can be varied by the magnetorheological properties of a liquid located between the components. For example, the present invention can optionally decrease the torque of a drive axle toward an output axle.

The magnetorheological transmission device according to the invention can be used in manifold technical fields, thus, e.g., on vehicles or industrial plants as a clutch or brake or for producing variable stops of a vehicle door. However, the invention can also be used, e.g., as a steering wheel lock on a steering column of automobiles or other two-wheeled vehicles or also as an anti-slip control, torque distributor, fan clutch, etc., in vehicles. Use as a joint on prostheses, artificial limbs, or in other technical fields is also possible.

Greatly varying clutches and the like are known in the prior art, in which, for example, a second component is brought into synchronous rotational movement with a first component via the activation of the clutch. For this purpose, for example, clutch plates, which are provided with a friction lining or the like, can contact one another in order to bring the second component to the speed of the first component through the initially grinding contact.

In addition to typical clutches and brakes with conventional friction linings, clutches are also known in which, for example, a magnetorheological fluid is provided between two components, which are used as clutch plates. Magnetorheological fluids have ultrafine ferromagnetic particles, for example, carbonyl iron powder distributed in an oil, for example. In magnetorheological fluids, spherical particles having a production-related diameter of 1 to 10 μm are used, wherein the particle size is not uniform. If a magnetic field is applied to such a magnetorheological fluid, the carbonyl iron particles of the magnetorheological fluid chain together along the magnetic field lines, so that the rheological properties of the magnetorheological fluid (MRF) are substantially influenced as a function of the shape and strength of the magnetic field.

A roller bearing, using which a steering column is mounted so it is rotatable, is known from DE 10 2004 009 906 B3. The legally prescribed minimum torque of greater than 100 Nm, by at least which a steering column must be blocked in the locked state, is to be achieved solely by the increase of the viscosity. Such a bearing is constructed as in the known prior art and has a bearing outer ring and a bearing inner ring and roller balls therebetween, which support the steering column and mount it so it is rotatable. A rheologically active substance is intercalated in the bearing intermediate space. A magnetic field is applied to increase the viscosity, whereby the traction between the bearing rings changes.

Experiments of the applicant in using such a bearing as a clutch have not resulted in a usable product. Roller bearings must have a slight play to allow the required load-bearing capacity and smooth running and to prevent deflection and therefore high wear. In the case of a routine roller bearing, which is typical for steering systems, having an internal diameter of 30 mm and an external diameter of 42 mm and roller bearings of approximately 4 mm diameter, the roller bearings have a total manufacturing-related scattered play of 6 to 20 μm (radial bearing clearance, tolerance class "normal" or P5, respectively). The radial running profile on each radial side of the roller ball is then half thereof, i.e., it moves between 3 μm and 10 μm. A greater running profile impairs the load-bearing capacity, increases the running noise, and results in substantially increased wear.

Since magnetorheological fluids have magnetically polarizable particles usually having a maximum diameter of 10 μm, it has been shown that such a roller bearing immediately blocks upon the addition of a drop of a magnetorheological fluid, even without application of a magnetic field and without bearing load. This is because a particle having 10 μm diameter cannot be pressed/rolled through a gap of 3 μm in magnetorheological fluids even without the application of an external magnetic field. In addition, agglomerations or chains of two or more particles also form or form because of this, so that a blockade of the roller bearing can occur even without an external field. In the normal state, a bearing load always acts on the bearing (radial or axial force), whereby the running profile of the roller bodies under load is decreased almost to zero and high surface pressures occur, whereby the roller bearing must be mechanically blocked, since then even the smallest particles having 1 μm diameter can no longer pass through between the roller bodies and the runway. The bearing becomes unusable and/or defective and the particles mechanically jam in the running gap. It also does not matter in this case if roller bearings having oversized base running profile, e.g., SKF production series C5 are used, except for the fact that increased bearing play decreases the load-bearing capacity and greatly shortens the service life.

Due to the continuous rolling of the roller bodies on the running surface in normal operation, i.e., with radial or axial load, very high surface pressures on the running surface sometimes result, which grind flat the interposed metal particles (>99% pure iron) of the magnetorheological fluid. In addition, the coating of the particles to protect against abrasion, sedimentation, and agglomeration can be damaged. Furthermore, the running surfaces can also be damaged. In practice, it has been shown that the particles thus changed mechanically stick together or cluster even without a magnetic field, whereby the magnetorheological fluid becomes unusable. This already occurs in the event of small mechanical compressions of the particles. In addition, the particle clusters thus formed can no longer be pressed through between the roller body and the runway, even in the case of large running profiles, and block the bearing.

In addition, conventional roller bearings are finally sealed, to prevent the entry of dust and hard particles and therefore decrease wear.

This also applies to DE 10 2006 034 966 A1, which discloses a roller bearing or linear bearing according to the prior art having improved localization of the lubricant by MR fluid.

A torque clutch is known from US 2008/0053776, in which magnetorheological fluid is placed between the rolling (meshing) gear wheels and a magnetic field is applied thereto. A transmittable torque of up to 1500 Nm is thus to be modulated. In order that such forces/torques can be transmitted, the tooth flanks must touch or the gear wheel play also goes to zero in this case, respectively, whereby the interposed MRF particles are damaged by the high surface pressure, as previously described in the case of the roller bearing of DE 10 2004 009 906 B3. The tooth flanks can jam and block without a magnetic field because of the particle size and the particle accumulation (cluster formation), respectively. The surface pressure and the flank play change continuously depending on the load (the torque) in the case of US 2008/0053776.

In the case of a known magnetorheological clutch having two clutch plates slightly spaced apart from one another, the two clutch plates, which are arranged at a suitable distance, can initially rotate relatively freely relative to one another without a magnetic field. However, a certain base torque can also be transmitted in the field-free state by shearing of the MRF depending on the slip of the clutch plates. If a magnetic field is activated perpendicularly to the clutch plates, the magnetorheological fluid chains together between the clutch plates and the two clutch plates are coupled to one another. The strength of the transmittable torque is dependent on various parameters, thus, e.g., the operating distance or the torque introduction distance, respectively, the operating surface, the number of the clutch plates, the relative speed, or the slip, and the magnetorheological fluid and in particular also the strength of the magnetic field. If the maximum transmittable torque is exceeded, the transmittable torque does not decrease to zero, but rather remains approximately at its maximum possible value, since chains of the particles of the magnetorheological fluid which are torn apart reform again immediately and thus become active again.

MRF clutches according to the prior art require large clutch plates having a diameter greater than 150 mm to reach high transmittable torques of, for example, greater than 50 Nm or more. Difficulties result therefrom due to the centrifuging out of the ferromagnetic particles because of the density difference in relation to the carrier medium. The fluid and the ferromagnetic particles can unmix.

A substantial advantage of magnetorheological clutches is that the wear is reduced. The load not only occurs on the outer surfaces of the clutch plates, but rather the energy is absorbed in the entire liquid volume.

The known magnetorheological clutches have the disadvantages of the high required magnetic field strength and a certain structural size, which results from the parameters of operating diameter, operating surface, and number of plates. A corresponding structural weight results therefrom, to be able to transmit the corresponding torques, which causes a poor torque/weight ratio. Strong magnetic fields which are generated by an electrical coil continuously require a large amount of electrical power, which is also undesirable.

BRIEF SUMMARY OF THE INVENTION

It is therefore the object of the present invention to provide a haptic interface and a magnetorheological transmission device, which in comparison to the prior art allows the transmission of higher forces or torques, possibly with smaller structural form and with low wear at the same time.

The objects of the invention are achieved by a device and a method as claimed. Preferred refinements of the haptic interface and the magnetorheological transmission device according to the invention are the subject matter of the dependent claims. Further advantages and features of the present invention result from the description of the exemplary embodiments.

There is provided, in accordance with the invention, a haptic interface, comprising:

a rotary element to be manually activated;

an integrated rotary encoder associated with said rotary element and disposed to interpret a rotation of said rotary element upon manual activation thereof; and a display, connected to said integrated rotary encoder, for displaying a given selected menu;

wherein at least one property of the haptic interface changes depending on a currently selected menu.

A magnetorheological transmission device according to the invention has at least two components which can be coupled, whose coupling intensity can be influenced. At least one channel is provided for influencing the coupling intensity. The channel at least partially contains at least one magnetorheological medium having magnetically polarizable particles, which can be influenced by a magnetic field. At least one magnetic field generating unit is provided for generating at least one magnetic field in the channel in order to influence the magnetorheological medium in the channel using the magnetic field. In this case, one component as the outer component surrounds in particular the other component as the inner component. Preferably, at least one of the two components is mounted via at least one separate bearing. A distance between the outer component and the inner component is preferably at least 10 times as great as a typical mean diameter of the magnetically polarizable particles in the magnetorheological medium. The magnetic field of the magnetic field generating unit can be applied in particular at least partially to the channel in order to optionally chain together the particles and/or release them.

In particular, a proportion by volume of polarizable particles in the magnetorheological medium is greater than 20%.

Preferably, there is in particular at least one magnetically conducting part that is at least partially flowed through by the magnetic field of the magnetic field generating device provided in the channel between the outer component and the inner component. There may also be a number of, in particular identical, magnetically conducting parts provided in the channel.

The part in the channel may be embodied as a rotating body and is embodied as a separate part between the first and the second components.

A free distance between the rotating body and the component is at least 10 times as great as a typical mean diameter of the magnetically polarizable particles in the magnetorheological medium. At least one acute-angled region, which contains or forms the magnetorheological medium, respectively, is provided between the rotating body and at least one component. The magnetic field of the magnetic field generating unit can be applied to the channel or at least a part thereof, in order to optionally chain together at least a part of the particles and wedge or release them with the rotating body.

In particular, the two components can be coupled to one another optionally and in a controlled manner.

The term coupling intensity is understood in the meaning of this application to mean the coupling force and/or the coupling torque between the two components. For example, if a linear force transmission is desired, the coupling intensity thus corresponds to the coupling force. If a torque is to be transmitted, the coupling intensity means the coupling torque.

The viscosity of the magnetorheological medium is preferably variable by the field, whereby the required displacement work for the relative movement of the components and/or the rotating bodies, which are movable relative to one another, can be influenced.

Displacement work is also understood to mean the displacement force which is necessary for displacing the medium in the case of a relative movement.

It is preferable for the at least one rotating body to be arranged between the two components. However, it is also possible that one of the components is implemented as the rotating body, which is at least partially provided on or in the channel.

Magnetorheological transmission devices according to the invention have many advantages. A substantial and surprising advantage of the magnetorheological transmission device according to the invention results from the substantially amplified effect of the magnetic field of the magnetic field generating unit in the channel. The acute-angled region which contains the medium acts as a lever and therefore somewhat like a strong mechanical lever transmission ratio, wherein the lever substantially amplifies the effect of the magnetic field by multiple times. Thus, either the field strength of the magnetic field generating unit can be reduced with the effect remaining the same, or the effect of the magnetic field can be amplified with the field strength remaining the same or the effect can even be increased with reduced field strength. The effect is in particular increased by multiple times by the acute-angled region which contains the medium when the magnetic field acts on the medium. In particular, the magnetic field acts at least sometimes on the acute-angled region, which contains or forms the magnetorheological medium, respectively.

Because the rotating body is arranged with a substantial free distance in relation to the at least one component, a macroscopic wedge can arise, which can be used to transmit strong clutch or brake torques. Substantial structural volume can be saved by the completely surprising multiplication of the effect. The utilized effect is based on the wedge formation (cluster formation) and not only the magnetorheological chaining of individual particles. The typical reaction time for the wedge formation requires several milliseconds, while individual particles are chained together according to the MRF effect already within approximately 1 ms. This time duration, which is multiple times longer, is due to the wedge formation. Such a substantial amplification of the effect was not expected. The longer reaction time of, e.g., 5, 10, or 20 ms is more than sufficient in many applications.

The channel can also be an intermediate space or a space which is open on four sides.

An acute-angled region of the channel is defined as the channel region which appears approximately to have an acute angle in at least one cross section through the shape of rotating bodies and components. The sides of the region do not have to be linear, they can also be curved and/or have another contour. The acute-angled region defines the part of the channel in which rotating body and components have the smallest distance to one another in particular or touch, respectively, and the adjoining region, in which the surfaces of rotating body and components move away from one another.

Under the effect of a magnetic field, the acute-angled region, which contains the magnetorheological medium, is formed, in which a substantially increased viscosity is present.

The invention allows a good torque to weight ratio, which can be greater than 100 Nm/kg.

A rotating body is preferably set into a rotational movement by a relative velocity in relation to at least one component. It is possible that the peripheral velocity of the rotating body is equal to the relative velocity in relation to the component. However, it is also possible that the peripheral velocity of the rotating body on its outer surface is greater than or less than the relative velocity. In particular, it is possible that the peripheral velocity of the rotating body on its outer surface is less than the relative velocity of the rotating body to the component.

The rotating body can be embodied to be substantially rotationally-symmetrical around at least one rotational axis. It is also possible that the rotating body is embodied to be rotationally-symmetrical around multiple rotational axes. For example, the rotating body can be embodied as a sphere or ellipsoid. It is also possible that the rotating body is designed as a cylinder, roller, or in general as a rolling body. In particular, an approximately cylindrical design has proven to be advantageous, since in the case of a cylindrical rotating body, for example, the acute-angled region, which contains the medium, forms over the entire width of the rotating body, so that this region is thus designed as substantially wedge-shaped. In these and other designs, the acute-angled region has a wedge shape.

However, it is not necessary for the rotating body to be embodied to be rotationally-symmetrical. Rotating bodies having elliptical or egg-shaped cross sections or rotating bodies having indentations like golf balls or having regular or irregular indentations and/or protrusions can also advantageously be used. The surface of the rotating bodies can be designed to be smooth, but does not have to be. Since the rotating bodies are not used for mounting and supporting the components relative to one another, a symmetrical and/or smooth surface is not necessary. Rotating bodies having rough and/or irregular surfaces can even be advantageous, since the wedge effect is amplified. Increased wear does not occur, because the rotating bodies are not used for mounting and transmitting load-bearing forces.

The amplification of the effect does not occur solely due to amplification or bundling of the magnetic field, but rather above all due to the particles clustered in front of the rotating bodies or rollers and the compaction thereof. Because of the magnetic field, the particles cannot move away and thus compact more rapidly to form a wedge. The wedge is externally controllable easily via switch. The advantage in the case of magnetorheological fluid such as MRF is that the wedge can disengage again by canceling out the magnetic field. The wedge can be influenced using the magnetic field—without mechanical movement or force introduction. It has proven to be advantageous for targeted influencing and reliable control that the free distance between the rotating body and the component is greater than a multiple of the particle diameter.

The diameter of the particles of the magnetorheological medium is in particular between 1 μm and 10 μm. The typical mean diameter of the particles of the magnetorheological medium is the arithmetically averaged diameter of the particles which are larger than the smallest percent and which are smaller than the largest percent. As a rule, this value corresponds to the mean value of the diameters of the largest and the smallest particle, i.e., 5.5 μm in the selected example. However, for example, if a very small number of even smaller particles are present, this does not change the typical mean diameter thus determined. This is also true if for example individual particles having 10.5 μm or 11 μm diameter are to be included.

The free distance between the rotating body and the component is preferably greater than 30 μm and in particular less than 300 μm. The typical mean diameter of the particles is preferably between 3 μm and 7 μm. The free distance between the rotating body and the component is preferably greater than 70 μm and in particular less than 250 μm.

The applicant reserves the right to claim protection for those magnetorheological transmission devices in which a free distance between the rotating body and the component is greater than the diameter of the typical largest magnetically polarizable particle. In particular, the free distance is greater than twice the diameter of the typical largest magnetically polarizable particle and can therefore be less than in the case of the otherwise identical above-described magnetorheological transmission devices according to the invention.

The acute-angled region advantageously wedges the components, which are freely movable relative to one another without a magnetic field, upon application of a magnetic field. A mechanical wedge in the form of a separate fixed part is not required for this purpose.

The acute-angled region is preferably provided between the body and one component in such a manner that the acute-angled region tapers relative to the rotating body in the direction of the relative movement of the component. If a cylindrical rotating body rolls on a flat surface of one component, the acute-angled region forms in a wedge shape in front of the rotating body. A wedge which is chained together as a whole, and which inhibits the relative movement of the rotating body to the component, arises due to the chaining together of the particles in the medium.

The rotating body and in particular each rotating body is particularly preferably embodied as a separate part between the first and the second components. It is then preferable for one component as the outer component to enclose the other component as the inner component. For example, a (drive) shaft can be provided as the inner component. The other or outer component can be used for braking, for example, and can radially enclose the shaft. The rotating bodies can be provided between the shaft and the outer component. It has been shown that rotating bodies which rotate around their own axis are substantially better for achieving the wedge effect. Finished bearing shells are not necessary. The transmission of a clutch or brake torque functions independently of the quality of the rolling surfaces.

At least one separate roller bearing is preferably provided for mounting the two components. In particular, the two components are mounted so they are rotatable, and preferably so they are rotatable relative to one another, via at least two additional roller bearings. The rotating bodies ensure, with the wedge effect, the transmission of the desired torques, while the roller bearing or bearings ensure the defined guiding and support of the two components, and the uniform running gap. Because of the substantial free distance or because of the play of the rotating bodies relative to the components, tilting of the components relative to one another can occur without the use of roller bearings.

In all designs, the free distance is preferably at least 10 times as great as the largest typical particle diameter. In specific embodiments, a free distance between approximately 5 times and in particular 10 times and 20 times the largest typical particle diameter has proven to be advantageous. In the case of larger free distances, the maximum transmittable torque is reduced again, since the wedge effect subsides. In the event of excessively small free distances, a blockade can occur even without a magnetic field. In addition, disengagement of the wedge after the shutdown of the magnetic field then cannot always be ensured.

The mean particle diameter is understood as the arithmetic mean of minimum and maximum particle diameters. Most MRF have magnetically polarizable particles which have a size distribution between approximately 1 μm and 10 μm. The mean particle diameter is 5.5 μm in this example. In the case of variable size distributions, the largest typical particle diameter is understood as a particle diameter, which only fewer than 1% of the particles exceed. The largest typical particle diameter is somewhat less than 10 μm in the mentioned example, so that 10 μm can be presumed to be the largest typical particle diameter here.

The free distance is preferably greater than $\frac{1}{500}$ and more preferably greater than $\frac{1}{250}$ and in particular greater than $\frac{1}{100}$ and particularly preferably greater than $\frac{1}{50}$ of a diameter of at least one rotating body, and in particular the free distance is less than $\frac{1}{10}$ and in particular less than $\frac{1}{20}$ of the diameter of the rotating body.

The free distance is preferably greater than $\frac{1}{300}$ of the external diameter of the inner component and/or greater than $\frac{1}{500}$ of the internal diameter of the outer component. The free distance is preferably greater than 30 μm and in particular less than 200 μm.

Variations by +/−20% are possible in the case of all numeric specifications. A particle is understood hereafter as a magnetically polarizable particle.

If oversize rotating bodies and/or shaft diameters are used, other distances can be advantageous. An advantage of this magnetorheological transmission device having at least two components, which can be coupled, is that the wedge formation is manufacturing tolerant, i.e., for example, manufacturing-related and installation-related differences in gap heights, surfaces, and dimensions and also thermal expansions or load-related shifts of components have a subordinate influence thereon and cause negligible torque or force differences.

For example, a structurally related change of the gap within certain system limits can also be recognized by sensors and worked out by field adaptation, for example.

In preferred designs, the rotating body is part of the first or the second component. This means that the rotating body, which is embodied as a rotating body, for example, is part of the first component and rolls on the second component, for example. The rotating body can also be without mechanical connection to both components, however.

In the acute-angled region, which is wedge-shaped, for example, the ferromagnetic particles chain together in the medium upon application of an external magnetic field and result in a locally more solid formation, which opposes the further relative movement between the rotating body and the adjacent component. The particles in the wedge-shaped part can be additionally compacted in the movement direction in front of the rotating body by the rolling movement of the rotating body. However, depending on the design of the rotating body, this compaction can also be performed by pitching, tilting, or other movements relative to a component.

For example, if the rotating body rolls on the surface of one component and such an acute-angled region forms in front of the rotating body, particles in the medium are thus entrained and set into rotational movement by the outer surface due to the rotational movement of the rotating body, wherein the hardening acute-angled region strongly opposes such a rotational movement, however. The acute-angled region in wedge shape results in a force on the rotating body away from the component. Such a force and a movement resulting therefrom can optionally also be used for fine alignment purposes. A rotational movement can preferably be converted into an axial displacement of the rotating body by the acute-angled region in wedge shape when the magnetic field is activated. The rotating body is thus more or less caused to float by the particles. It is also possible to provide the rotating body or a component with thread-shaped notches, for example, or to mount them at an incline relative to one another, in order to change the action direction of the resulting force or to further increase the achievable force transmission. A linear movement can thus be converted into a rotational movement using a type of threaded rod. The relative movement is inhibited by application of a field.

It is also preferable for the rotating body to be embodied as a separate part between the first component and the second component. Such a design can be particularly advantageous, since two acute-angled regions or wedge-shaped regions can occur between the rotating body and the two components. If the rotating body practically presses against the first component on one side and practically presses against the second component on the other side, acute-angled regions, which are subjected to the magnetic field of the magnetic field generating unit, form on both sides. The action is thus increased. It is not necessary for this purpose for the rotating body to press completely against the first component or the second component. A small gap remains between the rotating body and the respective component. The size of the gap is dependent, inter alia, on the properties of the medium. In particular, the size of the gap can be at least 5 times, and preferably at least 10 times or 20 times a typical or mean particle diameter.

The ferromagnetic particles consist in particular of carbonyl iron powder. The fluid can be an oil, for example.

It is also possible that magnetorheological and electrorheological media are used jointly. The use of other media which are influenced and chained together, for example, by corresponding fields is also conceivable. The use of media which change their rheological properties depending on other physical variables such as temperature or shear velocity is also possible.

The channel can be completely or also only partially filled with the medium. At least the acute-angled region of the channel is preferably filled with the medium.

In all embodiments, the first and/or second component can be embodied to be rotationally-symmetric. For example, the components can each be embodied as plates or cylindrical bodies, between which rotating bodies are provided, in order to increase the effect of the magnetic field of the magnetic field generating unit accordingly through the wedge effect.

In all embodiments, it is preferable for the magnetic field to run through the rotating body and in particular substantially transversely to the relative movement of the components relative to one another and from one component to the other component at least partially through the rotating body. Such a design has proven to be particularly effective, since the action of the magnetic field at the transition points from the rotating body to the walls of the channel is particularly strong. Depending on the acting magnetic field, it is therefore advantageous if the rotating body is at least partially magnetically conductive. In particular at least one component and in particular both components and/or the at least one rotating body are made at least partially of a ferromagnetic material. The permeability coefficient is preferably greater than 500. The permeability coefficient of the material, which is also referred to as the relative permeability, can also be 1000, 2000, or more. Rotating bodies made of ferromagnetic steel, such as ST37, are possible, for example.

Demagnetization of the material can be performed by a damped magnetic alternating field, so that a lower base torque is achieved without residual field.

In all embodiments, it is preferable for the magnetic field generating unit to comprise at least one permanent magnet and/or at least one coil. The use of one or more permanent magnets and one or more electrical coils is also possible.

It is possible and preferable to permanently change the magnetization of the permanent magnet by at least one magnetic pulse of an electrical coil. In such a design, the permanent magnet is influenced by magnetic pulses of the coil such that the field strength of the permanent magnet is permanently changed. The permanent magnetization of the permanent magnet can be set by the magnetic pulse of the magnetic field generating unit to an arbitrary value between zero and the remanence of the permanent magnet. The polarity of the magnetization is also variable. A magnetic pulse for setting a magnetization of the permanent magnet is particularly shorter than 1 min. and preferably shorter than 1 second and the length of the pulse is particularly preferably less than 10 ms.

As an effect of a pulse, the shape and strength of the magnetic field are permanently maintained in the permanent magnet. The strength and shape of the magnetic field can be changed by at least one magnetic pulse of the magnetic field generating unit. The permanent magnet can be demagnetized by a damped magnetic alternating field.

For example, AlNiCo is suitable as a material for such a permanent magnet with variable magnetization, however, other materials having comparable magnetic properties may also be used. In addition, it is possible to produce the entire magnetic circuit or parts thereof from a steel alloy with strong residual magnetism (high remanence) instead of a permanent magnet.

It is possible to generate a permanent static magnetic field using the permanent magnet, which can be overlaid by a dynamic magnetic field of the coil in order to set the desired field strength. The current value of the field strength can be varied arbitrarily by the magnetic field of the coil. The use of two separately activatable coils is also possible.

In all designs, it is preferable to provide at least one control unit. The use of an energy store, for example, a capacitor for storing at least a fraction of the required energy is also possible. At least one sensor or multiple sensors can be used for detecting relevant data, for example, the relative velocity of the components in relation to one another or the prevailing field strength and the like. It is also possible to use a temperature sensor as the sensor, which triggers an alarm if predetermined temperature conditions are exceeded, for example. A rotational angle encoder can advantageously be used to have data about the angular position of the components in relation to one another at any time.

In all designs, it is preferable for the permanent magnet to at least partially consist of a hard magnetic material, whose coercive field strength is greater than 1 kA/m and in particular greater than 5 kA/m and preferably greater than 10 kA/m.

The permanent magnet can at least partially consist of a material which has a coercive field strength less than 1000 kA/m and preferably less than 500 kA/m and particularly preferably less than 100 kA/m.

A magnetorheological transmission device according to the invention can preferably be embodied as part of a bearing, a brake, a clutch of an operating knob or control knob or a shock absorber, or the like. The use as a steering wheel lock is also possible, wherein continuous generation of the required field strength is ensured by a permanent magnet.

The rotating body and at least one component can touch on at least one point or at least one line. It is possible and preferable for the rotating body to be at rest relative to at least one component.

The rotating body can preferably move relative to at least one component, for example, in the form of a rotational or tilting movement.

The field strength can have a strong gradient depending on the respective distance between rotating body and components.

The field strength preferably increases in the acute-angled region between rotating body and components toward the region having the least distance.

An antitheft device in the form of a steering wheel lock to protect from vehicle theft is also possible for example with the invention. The steering column is blocked by a strong increase of the torque, for example. For this purpose, a permanent magnet can generate a permanent magnetic field, whereby a relative movement of the steering rod in relation to the steering column is made much more difficult. In conventional steering wheel locks, the locking bolts are sheared off in the event of an overload, after which free movement of the steering rod is possible. In contrast thereto, the provided force is maintained in the case of a solution according to the invention, even if it has been exceeded once.

A magnetorheological transmission device according to the invention in the form of a clutch or brake or the like, for example, has a substantially greater effect with a substantially smaller space requirement. The ratio of the installation space requirement to the prior art can reach or exceed a factor of 10. The use of a magnetorheological fluid as the medium in a magnetorheological transmission device according to the invention allows the cost-effective production of a clutch or a brake or the like. The need for maintenance can be substantially reduced, since few and simple parts are used. If necessary, the maintenance can be carried out by simple replacement of the magnetorheological fluid. The construction is simple and robust and power feedthroughs are not required. In addition, the power demand is less than in the prior art, because the wedge effect substantially contributes to influencing the relative movement of the components. MRF brakes or MRF clutches with a torque/weight ratio of >100 Nm/kg are thus possible.

In magnetorheological clutches or brakes according to the prior art, the magnetic field poles move relative to one another and generate shear forces (direct shear mode) in the interposed MR fluid. The shear forces vary depending on the magnetic field. No magnetic field means no or low shear forces (no chain formation in the MRF), maximum magnetic field means maximum shear forces and therefore maximum braking force or braking torque. In simplified form, magnetic field and shear forces are proportional.

In the present invention, through appropriate design of the individual components, dimensioning, and field introduction, very advantageous behavior which deviates therefrom can be provided. This advantageous behavior is expressed in that a substantially lower magnetic field, and therefore a lower current strength are required for maintaining the acute-angled embodiment or the MR fluid wedge than is required for the initial generation of the wedge. This is because the particle cluster no longer falls apart so easily once it has first been accumulated and has been quasi-mechanically compacted by the special movements fundamental to this invention under the influence of a correctly introduced magnetic field. As a result, for example, after a corresponding time for achieving this state, a braking torque can be maintained using the fraction of the magnetic field or electrical power (coil current), respectively, which is energetically advantageous.

If clutches having magnetorheological fluids according to the prior art are loaded beyond the maximum transmittable clutch torque, individual particle chains begin to break apart, whereby slip or slipping through results. The maximum clutch torque is maintained, however, or sometimes even slightly increases, and the clutch does not disengage. Depending on the application, this can be undesirable, for example, if a drillbit of a drill jams during drilling.

In the present invention, through appropriate design of the individual components, dimensioning, and field introduction, very advantageous behaviour which deviates therefrom can be provided. This advantageous behavior is expressed in that in the event a maximum force is exceeded between the moving parts, the wedge (material accumulation) generated by the magnetic field is suddenly pressed through the gap (material displaced) and the force therefore decreases suddenly at the same time. Because of the relative movement resulting therefrom and the high applied force, a new wedge does not form, whereby the relative force remains low. In the case of overload clutches, this behavior is very advantageous. The maximum force (triggering force) or the maximum torque (triggering torque) can be preset via the magnetic field.

Furthermore, unmixing, sedimentation, and centrifugal force problems are reliably prevented, since continuous mixing of the particles in the medium is achieved by the rotating rotating bodies.

Because of the substantially higher transmittable torques and forces, clutches, brakes, or the like having substantially smaller diameters can be implemented. Because of the small MRF channel height and the rotational movement of the rotating bodies, unmixing is practically not relevant in the case of the present invention.

The invention can be used in manifold ways, thus, for example, in prostheses as a joint for rotating components and as a damper in the case of a linear movement. The use on a vehicle door is also possible, in order to allow variable stops or defined standing open of the door. The use as a turn signal lever on vehicles or as an overload function on machine tools is also possible, in order to allow precise disengagement of the clutch if a limiting torque is exceeded.

A clutch according to the invention can be used to keep the torque or speed at the output independent of the drive, for example, in order to keep the speed constant or not to exceed a specific torque. It can also be used for intended purposes, in which a high torque is to be transmitted, thus, for example, in the torque allocation on a drivetrain.

Further possible uses are clutches in electrical drives in order to connect a load in a controlled manner, NC milling machines, wood processing machines, automation facilities, and use in industrial robots, sheet-metal processing machines, printing presses, textile machines, power looms, winding devices, hay balers, car loaders, electric window regulators, garage doors, roller blinds, etc., and in rapid milling cutters, food processors, mills, and the like.

For example, if a medium such as paper, thread, or the like is to be wound with uniform tension onto a roll, this can be achieved with the invention by varying the drive or braking torque in accordance with the diameter change of the winding roll. Further fields of use are adaptive brakes in fitness devices (e.g., rotation: bicycle trainer; treadmill; levers in weightlifting, rowing machines; linear movement: lifting weights, clamping the linear vertical adjustment of a saddle or office chair or the longitudinal adjustment of a steering column or a seat in a vehicle).

The invention can also be used in the case of a three-dimensional movement. The rotation and pendulum movement can thus be restricted or blocked by the MRF wedge. The acting torque is continuously adjustable and switching times in the range of a few milliseconds can be achieved. The construction is simple and no mechanically moving parts are required for varying the torque. A further advantage is that almost noiseless operation is possible. The additional costs are low and a magnetorheological transmission device according to the invention can be designed to be operationally reliable, for example, if a permanent magnet with remanence is used for setting a magnetic field. The wedge effect enormously amplifies the action, so that a smaller installation space is achievable.

In all designs, the rotating bodies do not have to be smooth, but rather can have rough or uneven surfaces.

The use of the invention as a haptic rotating knob is also possible. A rotating knob or a type of potentiometer can thus be practically implemented. The field of use is manifold and comprises, for example, controllers for crane operation or the like. The rotation can be controlled so it is stiffer depending on load. It can also be controlled as a function of the load height.

The use in "force feedback" applications or in "steer by wire" applications is also of interest. The use in operating elements in vehicles, car radios, stereo systems, etc., is also possible.

In all embodiments, it is also possible to use magnetic seals for sealing a device according to the invention, in addition to a seal with a sealing lip. The seal can be produced via a permanent magnet. Advantages of such a design are smaller base forces, freedom from wear, and the permissibility of greater manufacturing tolerances. In addition, defined overload behavior exists, since a defined breakthrough occurs if the overload is exceeded. It is possible to use such a seal in front of or behind a device according to the invention or to use it in front and behind.

A significant advantage of the magnetic seal is the very low friction; however, it can be necessary to use still a further seal, since such a seal possibly only holds back MRF particles and permits oil as the base liquid to pass through the gap over time, for example. Therefore, such a magnetic seal can be used as an outer seal, in order to hold back MRF particles. A further classic seal only seals off the carrier medium, for example.

A movement of the magnet can be used to achieve lubrication in the MRF, as well as material transport and cooling, for example, via hydrodynamic effects. In addition, a flow away from the seal can be achieved and pressure differences can be dissipated.

In order for example to set the play between two parts or to remove play from a design and to compensate for manufacturing tolerances, for example, a force or an axial force and/or a radial force can be used, which is induced by an MRF wedge effect.

The running profile of ball bearings or roller bearings or needle bearings can be reduced down to zero by the wedge or the buildup of a wedge or an MRF layer. This functions very well in particular with inclined contact ball bearings or tapered roller bearings, since the play is preset or settable by the design here. If there is a large amount of play, axial travel can be forced during the buildup of the wedge. In this application, the MRF wedge effect is not used as a clutch or as a brake, but rather to set the bearing play.

In refinements, it is possible for a radial or axial force, for example of an inclined contact ball bearing, to act against a spring or a yielding element, such as for example rubber. It is not only possible to work between two fixed delimitation surfaces, but rather also for one fixed stop and one spring-loaded stop to be used. A greater adjustment range and lower spring stiffness can thus be achieved.

The MRF wedge or an MRF wedge can be generated by a magnetic field of a magnet. A permanent magnet can be adjustable by hand or it is also possible to displace or rotate the permanent magnet or a shield by hand or using actuators, in order to increase or decrease the field strength in the relevant region. An arbitrary part of the magnetic circuit can be moved relative thereto in order to influence the magnetic field acting in the MRF wedge.

A mechanical fine or coarse alignment and therefore also setting of the braking effect can be possible. Such a setting can be provided, for example, to compensate for physical variables such as temperature, pressure, speed, or the like. It is also possible to compensate for tolerances or installation inaccuracies.

In all embodiments, it is preferable to provide a settable permanent magnetic field strength via remanence. In preferred embodiments, a bearing having a magnetorheological transmission device according to the invention has no or only minimal residual magnetism (remanence) itself. Otherwise, a position-dependent counterforce of different strengths can occur, since the parts move in relation to one another.

In advantageous designs, the remanence material is to be arranged in a general region of the bearing, which is permeated by the magnetic field in a particularly position-independent manner, thus, for example, the inner shaft or the outer envelope, etc.

However, it is also preferable to use the effect of the position-dependent magnetization, in that, e.g., the inner running surface having remanence is used in order to generate specific detent torques, for example. This can be performed, for example, for haptic feedback about variable detent torques with respect to their strength, the rotational angle, or the end stop or the like. Not all bearing balls have to be ferromagnetic, depending on the desired setting capability.

It is also possible to provide a magnetorheological transmission device with a design deviating from the classic bearing construction. For example, the direction of the magnetic field can also be aligned at least partially or completely approximately parallel to the axis. At least partial alignment parallel to the rotational direction or movement direction or in the tangential direction is also possible. It is also possible that the entire magnetic circuit is arranged nearly or completely in the interior.

The material of the magnetorheological transmission device does not have to be completely ferromagnetic, depending on the desired application or magnetization, respectively. It can be advantageous if individual parts of the magnetorheological transmission device are not ferromagnetic or are only partially ferromagnetic, respectively.

Depending on the application, it is also conceivable to manufacture at least one part from different materials, to obtain locally differing magnetic properties.

One possible embodiment is a rotating knob with an integrated rotary encoder and a magnetorheological transmission device with wedge effect. The position or the rotational angle of the rotating knob can be determined via the rotary encoder and the rotational resistance can be varied in a wide range. Thus, for example, a haptic interface with variable detent torques and arbitrarily settable end stop can be constructed, which changes its properties depending on the currently selected menu. A low or high torque and/or small or large pattern/ripple and also a variable pattern—depending on the menu to be operated—can be set. The curve of the torque increase and decrease can be set or varied depending on the situation, for example, as a square-wave, sinusoidal, sawtooth, or arbitrary curve. A stop can also be simulated. The stop can be hard or can have a predefined or situation-dependent torque curve.

The rotating knob as one component is preferably fixedly connected to the shaft as the other component, which is in turn mounted so it is rotatable in the housing. The relative movement or relative position is detected via a rotary encoder, for example, via a magnetic, optical, or (via buttons) mechanical incremental encoder. A potentiometer with slip contacts can also be used, but only specific rotational angles are typically permissible using such a potentiometer.

A sealing ring is advantageous, so that the magnetorheological fluid remains in the housing. The seal can also only consist of permanent magnets or a combination of permanent magnet and typical seal.

The inner region, i.e., the volume enclosed by seal and housing, is at least partially filled with a magnetorheological fluid.

The housing is preferably designed as a pot, i.e., it is closed on one side. Only one sealing ring is thus required. A continuous shaft (two-sided shaft) is also conceivable.

The coil can generate a magnetic field, wherein the magnetic circuit is closed via the housing, the shaft, and the magnetorheological transmission device. The magnetic field required for the wedge effect can thus build up in the magnetorheological transmission device. The coil is advantageously fixedly connected to the housing, which makes the cable guiding easier.

The construction is robust and can be designed so that almost no magnetic scattered fields are generated outside the housing. However, many other construction variants are conceivable, which can have specific advantages depending on the application.

For example, the coil can also be arranged outside the housing, wherein the magnetic field then acts through the housing on the magnetorheological transmission device. No mechanical connection is necessary between coil and housing, the coupling of the magnetic circuits is sufficient to influence the magnetorheological transmission device in the housing. In particular, the coil does not have to be permanently located on or in proximity to the housing and can be designed such that it can be removed from the housing as a separate unit. Permanent magnets can also be provided in the magnetic circuit.

In a preferred embodiment, the rotating knob can be electromagnetically driven, for example, and can also actively exert a force (force feedback) to be able to statically generate a specific counter torque. In this design, a better torque to installation space ratio is achieved than in many designs according to the prior art. In addition, the production costs are low because of the simple construction, since, for example, the rolling surfaces of the components do not have to be high-precision in haptic applications and also typically do not have to withstand high speeds and a large number of revolutions. In general, the magnetorheological transmission device described here has a very low base friction (OFF state). A battery and a control command transmission unit (radio, WLAN, Bluetooth, antenna) are preferably also integrated in the actuator or rotating knob, respectively. The haptic knob can be placed anywhere and does not require a wired control connection or power connection. The MRF wedge principle requires very little current (power) in relation to the torque. It is therefore also well suitable for battery operation or for wireless power supply. Both the required power and also control commands and, for example, measured values from sensors such as rotational angle can also be transmitted wirelessly.

A preferred embodiment manages without a battery and receives the power required for the function by means of inductive coupling. Embodiments are also particularly preferred which acquire the power required for operation directly from the environment and buffer it locally (energy harvesting). Thermoelectric generators, solar cells, elements which convert vibrational energy into electrical power, and others, as well as corresponding local energy stores are possible for the energy conversion. It is also conceivable to use the movement of the magnetorheological transmission device itself for the power generation.

If a magnetic field is applied to the magnetorheological transmission device according to the invention at least partially via a permanent magnet, and the magnetization of the magnetic field is permanently changed by at least one magnetic pulse of at least one electrical coil, several advantages result. In specific cases, for example, through the utilization of the remanence and the pulsed operation of a coil, which does not always have to be energized, weight and space advantages can be achieved. The wires of the coil can be dimensioned thinner and lighter, because they must respectively only be energized for a short operating time. Advantages can thus result in the case of weight, power demand, space requirement, and costs.

Therefore, it can be advantageous in specific applications that due to the pulsed operation of the electrical coil, it can be implemented significantly smaller than if it must be designed for 100% activation time. The heating of the coil typically does not play a role in pulsed operation, since short-term power loss peaks are buffered by the intrinsic heat capacity of the coil and the parts surrounding the coil. Very high current densities in the windings can thus be tolerated or thinner lines can be used, as long as the mean power loss remains acceptable over longer periods of time.

In the case of a smaller coil, the resulting magnetic circuit surrounding the coil can also typically be smaller, because of which a comparatively large amount of installation space, material, weight, and costs can be saved. Only the power expenditure for a single pulse increases, which can be very well tolerated depending on the application, however. Overall, a large amount of power can nonetheless be saved in comparison to a continuously energized coil.

In all designs, it can be possible to implement the power supply in a wireless manner. The power can be supplied, for example, from the power source to the power electronics or from the power electronics to the coil, respectively, via an electrical, magnetic, or electromagnetic coupling, for example, a radio link. In the application in a bicycle, the power can be supplied externally via a docking station, for example. The power supply via a power source on a bicycle, for example, to all consumers (forks, rear shock absorbers, display) is also possible. The power can also be supplied similarly in the case of a ski boot, ski, mobile telephone, or to the sensors.

A power supply via radio can possibly have worse efficiency than typical wiring. In addition, the power transmission and its range can be limited. However, such advantages do not interfere depending on the application. It is advantageous that no wear of the contacts occurs. The power transmission is typically secure from incorrect polarity and short-circuit-proof, because only limited power is present on the secondary side. Furthermore, wire breaks are not possible and the device is more movable as a whole.

In such designs, however, it is advantageous to buffer the power for at least one pulse in a capacitor or energy store. The power supply of the system can thus have a smaller power, since short-term power peaks of a pulse can be absorbed by the capacitor. In addition, a discontinuous or pulsed power supply can also be used.

One possible construction step of the present invention is a fully autonomous system, which is wirelessly supplied with power. For example, application in a bicycle is conceivable, wherein the system is supplied with power by at least one small magnet on a tire.

In general, arbitrary "energy harvesting" units can thus be used for the power supply, for example, solar cells, thermoelectric generators, or piezocrystals. Elements which convert vibrations into energy can thus also be used very advantageously for the supply.

An embodiment is also conceivable similar to an electric toothbrush, in which the power supply is performed by inductive coupling. For example, the battery can be inductively charged, without damaged cables or corroded or soiled contacts obstructing the charging procedure. Power can be transmitted via a magnetic resonance over longer distances.

The power supply of the remanence pulse can be performed via induction, as in the case of electric toothbrushes. The combination of the MRF wedge principle with remanence is particularly power saving and advantageous.

A loudspeaker or a noise generating unit can also be integrated or assigned. This is advantageous, because the rotating knob as the MRF wedge knob is mechanically noiseless per se. Both the rotation without and also with pattern and/or the virtual stops are noiseless per se. The generation of the MRF wedge for a torque increase or to generate a pattern is also noiseless per se. By means of the noise source, such as a loudspeaker or a piezo loudspeaker, for example, a click can be associated with the virtual pattern at each detent position. The type, volume, and duration of the noise can be individually assigned, but can also be changed or turned off if the user wishes.

Therefore, the torque, the pattern, the stops, and the noise are programmable or adaptive, respectively. The noises can also be generated via external loudspeakers, for example, standard loudspeakers in the automobile or the loudspeakers of the stereo system in the home.

The haptic knob can therefore practically replace the mouse wheel of a computer mouse. In the case of the pattern, not only the angle interval of the pattern can be settable, but rather also its curve shape, thickness, etc. A pattern characteristic curve can therefore more or less be predefined.

The haptic rotating knob can also be installed on an operating panel or on a display screen. In order that the display screen does not have to be removed for fastening the knob, it can consist of an upper part on the display screen and a lower part below the display screen. Data transmission via induction or the like, for example, is preferably provided. The display screen can thus be produced more cheaply as a surface.

It is also possible that an MRF haptic knob can also be pressed. The pressing can also act through an MRF, whose properties are variable via a magnetic field.

The display screen indicates the information to be set, which changes depending on the application. The function of the haptic knob adapts itself thereto. In one case, adjustment is made by means of a pattern (for example, setting the volume; a volume scale appears on the display screen, which can also have a logarithmic scale).

In another case, an adjustment can be made between two positions without a pattern, but with variable torque, thus, for example, between the clock setting 8:00 and the clock setting 16:00, wherein an increasing torque can be provided in each case before the end position. The pattern can also be used for approaching defined positions, for example, if a name input is requested.

The display screen can also be embodied as a touchscreen. Menu points can thus be rapidly selected and fine settings can be made by means of the rotating actuator. For example, it is not desirable in the case of automobiles to control the volume of the radio via touchscreen, since the driver must otherwise always look down for a long time at what and where he is currently adjusting, which distracts him. He can find the rotating actuator with a brief glance or even without looking at it.

The adjustment using a mechanical actuator is also simpler and safer than via a touch display when bicycling, for example. This is true in particular even if the bicyclist is wearing gloves, for example, whereby the operation of a touch display is more difficult or even impossible.

A combination of a display screen or touch display and a mechanical rotating actuator with variable torque/pattern is also possible. Such input devices can also be advantageous outside the motor vehicle, thus, for example, in the case of controllers for industrial plants, remote controls for televisions or radio vehicles such as toy helicopters, for example, and on PCs and games consoles, and control consoles for military applications (drone aircraft, rockets).

It is also possible that a haptic rotating knob with a display replaces the current computer mouse.

It is possible that the rotating knob or the actuator can be countersunk in the normal state and is only extended if needed.

It is also possible to embody such a structural unit as a slide regulator, in particular in combination with a linear MRF wedge unit.

It is also possible to equip a magnetorheological transmission device with one or more poles and one or more protrusions. In all designs, it is possible that protrusions or the like, which protrude from one component in the direction toward the other component, for example, are provided between the two components of the magnetorheological transmission device.

Such a design is possible and preferred both in the case of rotational mobility and also in the case of linear mobility of the two components to one another.

Only one protrusion can be provided or multiple protrusions can be provided. It is possible that a ball or a roller or another rotating body, which is at least partially accommodated by the protrusion, is arranged on at least one protrusion.

If protrusions are provided on one component, it is preferable for at least one pole or at least one magnetization unit or at least one magnet or one coil to be provided on the other component. The number of the magnetization units or poles can be 1 or can also be greater.

The shape of the protrusions can fundamentally be arbitrary and can be semicircular, tapered, or blunt, for example. The receptacle region of rotating bodies is preferably accordingly embodied as rounded.

One or more magnetization units or poles can be embodied as electric coil plus core or as a permanent magnet or can consist of remanence material or a combination thereof.

The intervals between individual protrusions and/or magnetization units are preferably approximately uniform, but can also be arbitrary.

The depth, i.e., the radial extension or the axial extension of individual protrusions or magnetization units to others can be different.

The field strength which is applied to or acts on the individual magnetization units can in particular also vary at the same time.

The speed of the rotating bodies does not have to be equal to the rolling speed, it can also deviate therefrom, for example, by step-down or step-up transmissions. The inner part which is embodied by the protrusions, for example, as star-shaped, can be mounted off-center to the outer part.

One application of such a magnetorheological transmission device can be, for example, as a haptic knob with pattern or in furniture and drawer guides with positions.

The magnet or each magnetization unit or the inner part and/or the outer part can also consist of remanence material.

If it is used on a steering column, the device can be used for the purpose of braking the steering around the middle location, so that, for example, in the case of power steering which is intrinsically smooth, the steering becomes stiffer, which is advantageous during straight-ahead travel on a freeway, for example. A magnetorheological transmission device can brake such smooth steering and thus increase the driving comfort, through a torque which is adapted to the respective situation or user.

It is also possible to make other steering procedures safer, for example, by implementing end stops using a magnetorheological transmission device. Therefore, functions are also made possible in the case of hydraulic steering systems, which could previously only be implemented via electronic steering systems.

Since magnetorheological fluids chain together very rapidly upon the application of a magnetic field, it can be sufficient in the normal state, for example, during car driving, if the magnetic field is turned off. It is typically entirely sufficient to only turn on the field when a first rotational angle change is initiated. A significant amount of power can thus be saved.

Alternatively thereto, a base torque can be implemented with remanence. When a rotational angle change is registered, a dynamic magnetic field can be built up, which can also pulsate to generate a virtual pattern.

In all designs, it is possible to implement an adaptive door brake, for example. For this purpose, a parking distance can be measured in the case of a motor vehicle during parking, for example. The distance to the adjacent motor vehicle can be calculated from the data. The maximum angle to which the door can be opened can in turn be calculated therefrom and the opening procedure can be braked accordingly upon reaching this angle or even before.

For this purpose, the sensor or the sensors for measuring the distance from the vehicle during parking can be used, so that separate sensors are not necessary. It is also possible to perform the control so that the door initially opens easily and then a pattern occurs, which becomes finer and finer. A haptic display for door openers would thus be practically implemented, which indicates when the stop is approached.

It is also possible to hold open doors, windows, or the like at specific angles. This can be implemented in the case of motor vehicles or also in the case of furniture, for example.

In embodiments in which the remanence is utilized, the magnetic field for the remagnetization can be externally applied. A corresponding coil, which acts through a cylinder, for example, can be used for the remagnetization.

In the method according to the invention, the coupling intensity of at least two components, which can be coupled is influenced, using a magnetorheological transmission device, wherein the coupling intensity is influenced in at least one channel which contains a magnetorheological medium with magnetically polarizable particles, which can be influenced by a magnetic field, and wherein at least one magnetic field is generated in the channel using at least one magnetic field generating unit in order to influence the magnetorheological medium in the channel using the magnetic field. At least one rotating body is provided in the channel and a free distance between the rotating body and the component is greater than 10 times the diameter of the typical mean magnetically polarizable particle. At least one acute-angled region which contains the magnetorheological medium is provided between the rotating body and at least one component. The magnetic field of the magnetic field generating unit is at least temporarily and at least partially applied to the channel, in order to optionally chain together the particles and/or wedge or release them with the rotating body.

Further advantages and features of the present invention result from the exemplary embodiments, which are explained hereafter with reference to the appended drawings.

DESCRIPTION OF THE INVENTION

With reference to the appended figures, exemplary embodiments of magnetorheological transmission devices 1 according to the invention are explained hereafter, wherein identical or similar parts are provided with the same reference signs.

Figure 1:
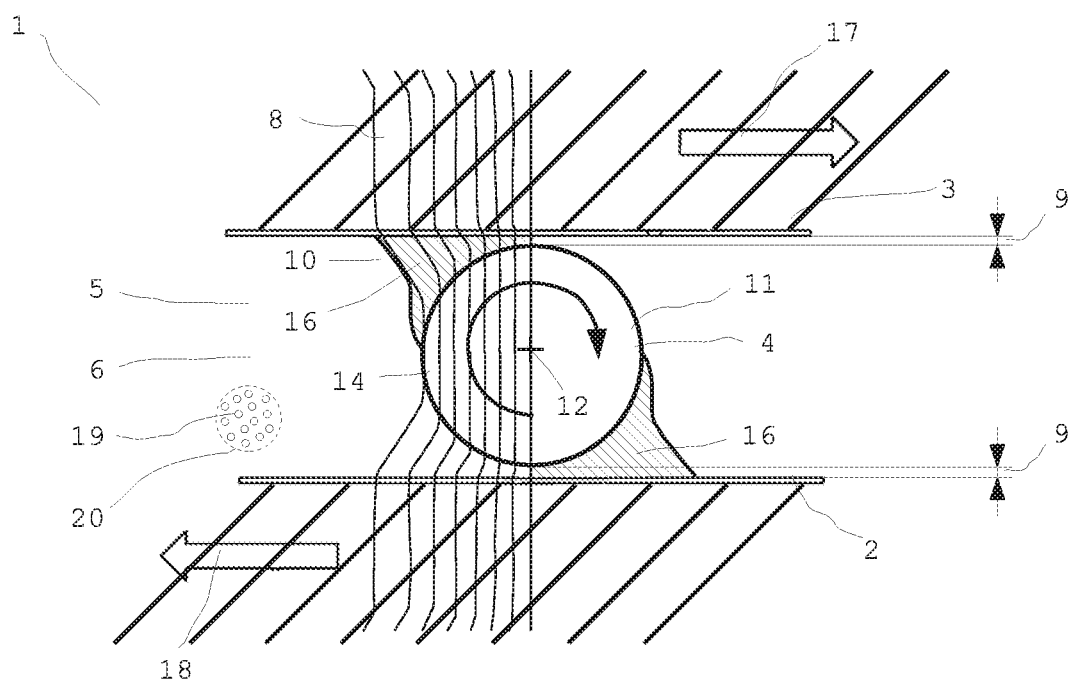
FIG. 1 shows a very schematic view of a magnetorheological transmission device according to the invention in cross section.

FIG. 1 shows a very schematic cross-sectional view of a magnetorheological transmission device 1 according to the invention for influencing the force transmission between two components 2 and 3. A rotating body 11 is provided as a separate part 4 between the two components 2 and 3 in FIG. 1. The rotating body 11 is embodied here as a ball 14. However, it is also possible to embody rotating bodies 11 as cylinders or ellipsoids, rollers, or other rotatable rotating bodies. Rotating bodies, which are not actually rotationally-symmetrical, for example, a gear wheel 34 or rotating bodies 11 having a specific surface structure can also be used as rotating bodies. The rotating bodies 11 are not used for the mounting in relation to one another, but rather for transmitting torque.

A channel 5, which is filled here with a medium 6, is provided between the components 2 and 3 of the magnetorheological transmission device 1. The medium is a magnetorheological fluid 20 here, which comprises an oil as the carrier liquid, for example, in which ferromagnetic particles 19 are present. Glycol, grease, and viscous materials can also be used as the carrier medium, without being restricted thereto. The carrier medium can also be gaseous or the carrier medium can be omitted (vacuum). In this case, only particles which can be influenced by the magnetic field are poured into the channel.

The ferromagnetic particles 19 are preferably carbonyl iron powder, wherein the size distribution of the particles depends on the specific usage. A distribution of particle size between 1 and 10 µm is concretely preferable, wherein larger particles of 20, 30, 40, and 50 µm are also possible. Depending on the application, the particle size can also become significantly larger and even advance into the millimeter range (particle beads). The particles can also have a special coating/sheath (titanium coating, ceramic sheath, carbon sheath, etc.), so that they can better withstand the high pressure loads occurring depending on the application. The MR particles can be produced not only from carbonyl iron powder (pure iron), but rather also from special iron (harder steel), for example, for this application.

The rotating body 11 is set into rotation around its rotational axis 12 by the relative movement 17 of the two components 2 and 3 and practically runs on the surface of the component 3. The rotating body 11 simultaneously runs on the surface of the other component 2, so that a relative velocity 18 is present there.

Strictly speaking, the rotating body 11 has no direct contact with the surface of the component 2 and/or 3 and therefore does not roll directly thereon. The free distance 9 from the rotating body 11 to one of the surfaces of the component 2 or 3 is, for example, 140 µm. In a specific design with particle sizes between 1 µm and 10 µm, the free distance is in particular between 75 µm and 300 µm and particularly preferably between 100 µm and 200 µm.

The free distance is in particular at least 10 times the diameter of a typical mean particle diameter. The free distance is preferably at least 10 times the size of a largest typical particle. Due to the lack of direct contact, a very low base friction/force/torque results during the relative movement of the components 2 and 3 in relation to one another.

If a magnetic field is applied to the magnetorheological transmission device 1, the field lines form depending on the distance between the rotating bodies 11 and the components 2, 3. The rotating body consists of a ferromagnetic material made of ST 37 here, for example. The steel type ST 37 has a magnetic permeability pr of approximately 2000. The field lines pass through the rotating body and concentrate in the rotating body. A high flux density in the channel 5 prevails on the rotating body at the radial entry and exit surfaces of the field lines here. The inhomogeneous and strong field there results in local and strong crosslinking of the magnetically polarizable particles 19. The effect is strongly increased by the rotational movement of the rotating body 11 in the direction toward the forming wedge in the magnetorheological fluid and the possible brake or clutch torque is greatly increased, far beyond the amount which can normally be generated in the magnetorheological fluid. Rotating body 11 and component 2, 3 preferably consist at least partially of ferromagnetic material, because of which the magnetic flux density is higher the smaller the distance between rotating body 11 and component 2, 3. A substantially wedge-shaped region 16 thus forms in the medium, in which the gradient of the magnetic field increases strongly toward the acute angle at the contact point/the region of the smallest distance.

In spite of the distance between rotating body 11 and component 2, 3, the rotating body 11 can be set into a rotational movement by the relative velocity of the surfaces in relation to one another. The rotational movement is possible without and also with an active magnetic field 8.

If the magnetorheological transmission device 1 is subjected to a magnetic field 8 of a magnetic field generating unit 7 (not shown here in FIG. 1), the individual particles 19 of the magnetorheological fluid 20 chain together along the field lines of the magnetic field 8. It is to be noted that the vectors shown in FIG. 1 only show the region of the field lines which is relevant for the influence of the MRF 20 in a roughly schematic form. The field lines enter into the channel 5 substantially normally to the surfaces of the ferromagnetic parts and above all do not have to run linearly in the acute-angled region 10.

At the same time, some material is also set into rotation by the magnetorheological fluid 20 on the periphery of the rotating body 11, so that an acute-angled region 10 forms between the component 3 and the rotating body 11. On the other side, an identical acute-angled region 10 arises between the rotating body 11 and the component 2. The acute-angled regions 10 can have a wedge shape 16 in the case of cylindrical rotating bodies 11, for example. Because of the wedge shape 16, the further rotation of the rotating body 11 is obstructed, so that the effect of the magnetic field on the magnetorheological fluid is amplified, since a stronger cohesion of the medium 6 in the region results due to the active magnetic field within the acute-angled region 10. The effect of the magnetorheological fluid in the accumulated cluster is thus amplified (the chain formation in the fluid and therefore the cohesion or the viscosity), which makes the further rotation or movement of the rotating body 11 more difficult.

Substantially larger forces or torques can be transmitted by the wedge shape 16 than would be possible using a comparable construction which only utilizes the shear movement without wedge effect.

The forces which are transmittable directly by the applied magnetic field only represent a small part of the forces transmittable by the device. The wedge formation and therefore the mechanical force amplification may be controlled by the magnetic field. The mechanical amplification of the magnetorheological effect can go so far that a force transmission is possible even after an applied magnetic field is turned off, if the particles have been wedged.

It has been shown that a substantially greater effect of a magnetic field 8 of a specific strength is achieved by the wedge effect of the acute-angled regions 10. The effect can be amplified multiple times. In a concrete case, an influence of the relative velocity of two components 2 and 3 to one another which was approximately 10 times as strong as in the prior art was observed in MRF clutches. The possible amplification depends on different factors. It can optionally be amplified further by a greater surface roughness of the rotating bodies 11. It is also possible that externally protruding projections, which can result in still stronger wedge formation, are provided on the outer surface of the rotating bodies 11.

The wedge action or the wedge effect is distributed flatly on the rotating body 11 and the components 2 or 3.

Figure 2:
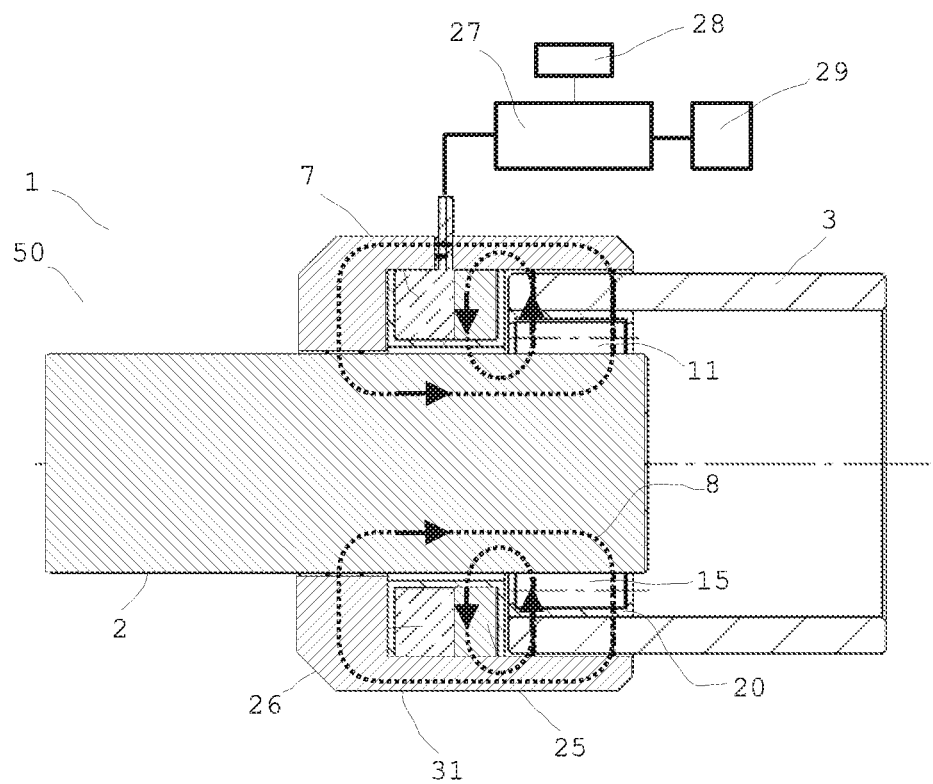
FIG. 2 shows a magnetorheological transmission device according to the invention embodied as a clutch.

FIG. 2 shows a clutch 50 having a magnetorheological transmission device 1 according to the invention, wherein the components 2 and 3 are embodied as rotating parts here. The magnetic field generating unit 7, which comprises a coil 26 and a permanent magnet 25 here, is provided on a stationary component 31. The coil 26 is connected to a control and/or regulating unit 27. A permanent magnetic field 8 can be applied using the permanent magnet 25, wherein the magnetic field active in the channel can be modulated by activating the electrical coil 26. The active magnetic field can thus be decreased or amplified.

In the exemplary embodiment here, it is preferable for the coil 26 to be embodied to deliver strong magnetic pulses, using which the permanent magnet 25 is permanently variable. Through short-term pulses in the range of 0.1 to 1000 ms, the magnetization of the permanent magnet 25 can be intentionally varied between zero and its remanence. Following the pulse, the magnetic field strength of the permanent magnet 25 is maintained unchanged for a practically arbitrarily long time. Through suitable modulation of the pulses, the active field strength of the permanent magnet 25 can thus be set arbitrarily frequently, so that a specific field strength can be generated even without continuous power supply.

In order to also be able to vary the strength of the magnetic field of the permanent magnet 25 without continuous power connection, an energy store 28 can be provided, which is embodied as a capacitor and keeps the power ready for at least one pulse, for example. For the targeted regulation of the field strength of the permanent magnet 25, at least one sensor 29 can be provided, which measures the active magnetic field strength, for example. It is also possible that the sensor detects further data, such as the torque, the speed, the relative velocity, the rotational angle of the two components 2 and 3 in relation to one another, or the prevailing temperature or the like. If necessary, corresponding steps can be initiated, for example, if the permissible temperature of the magnetorheological transmission device 1 is exceeded.

The use of a mechanical setting device is also conceivable, in the case of which the field strength in the channel can be changed by moving the magnet, pole shoes, or shielding plates, for example. This mechanical setting can also be used in combination with a Bowden cable and/or an electrical adjustment, for example, if the permanent magnet sets a base force as the operating point and a controller can change the force around this operating point by means of the coil.

Figure 3:
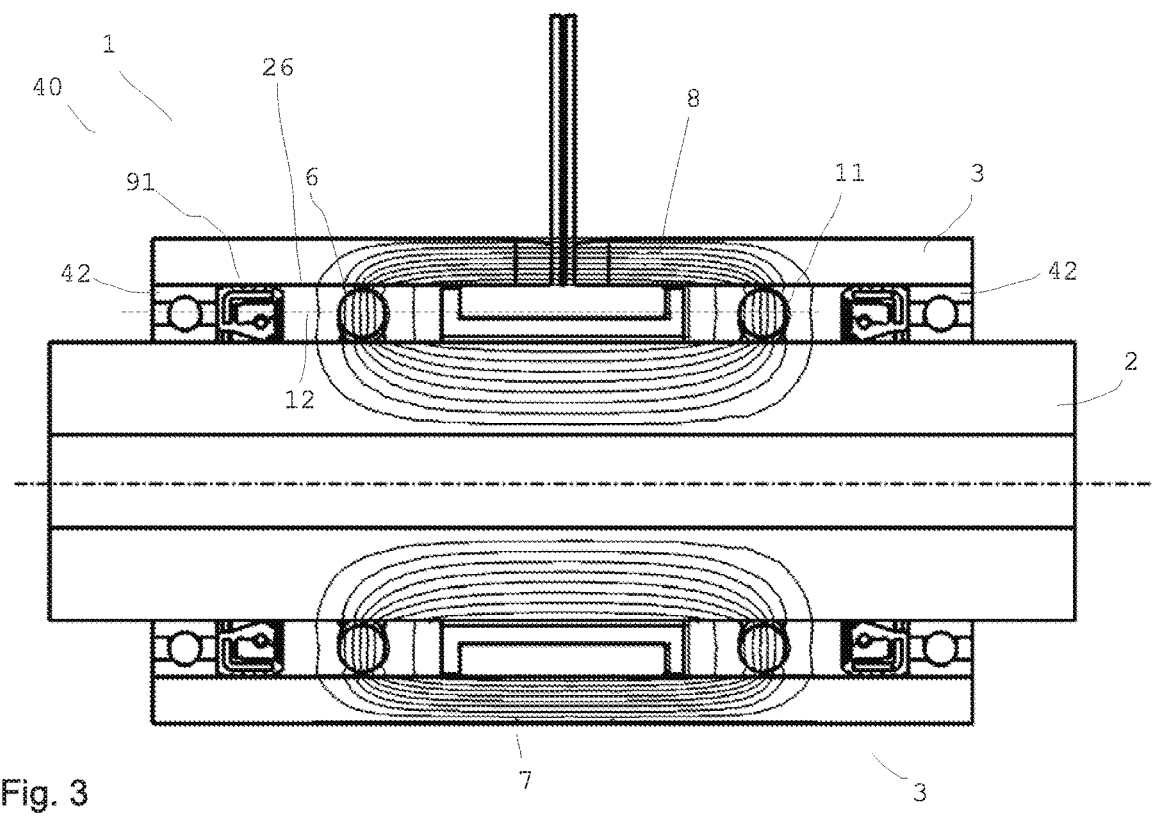
FIG. 3 shows a magnetorheological transmission device embodied as a brake.

FIG. 3 shows a magnetorheological transmission device 1 according to the invention, which is embodied as a brake 40. The magnetorheological transmission device 1 has a component 2 embodied as a shaft, whose rotational movement relative to the stationary component 3 can be influenced. Bearings 42 for the rotatable mounting of the components 2, 3 are provided between the stationary component 3 and the rotatable component 2. The rotating bodies 11 between the components 2 and 3 are embodied here as balls 14 and are enclosed by the medium 6 or the magnetorheological fluid 20, respectively. Seals 91 are provided between the rotating bodies 11 and the bearings 42 to protect the bearing 42 and to prevent the escape of magnetorheological fluid.

A magnetic field generating unit 7 embodied as a coil, for example, is used for the targeted control of a magnetic field 8, which also extends through the rotating bodies 11 and is aligned there substantially transversely and here even perpendicularly to the relative movement of the two components 2 and 3 in relation to one another. When the magnetic field 8 is turned on, the rotational movement of the rotating bodies 11 causes chaining together of the particles 19 in the magnetorheological fluid 20, whereby the acute-angled regions 10, which substantially obstruct a further rotation of the component 2 relative to the component 3, arise on each individual rotating body 11. The effect of the magnetorheological fluid is thus substantially amplified.

The MRF wedge housing can be pushed over an (existing) drive shaft, this drive shaft is then braked depending on the active magnetic field 8, wherein the MRF wedge results between the shaft surface and the rotating bodies 11. A very simple construction therefore results. Normal brakes or clutches typically require a plate or other flanged parts for this purpose and have a fixed shaft position when viewed axially. In the case of an MRF wedge housing according to the invention, the shaft can be axially displaced without this affecting the wedge effect. A separate running ring does not have to be affixed to the component 2 used as the shaft.

Figure 4:
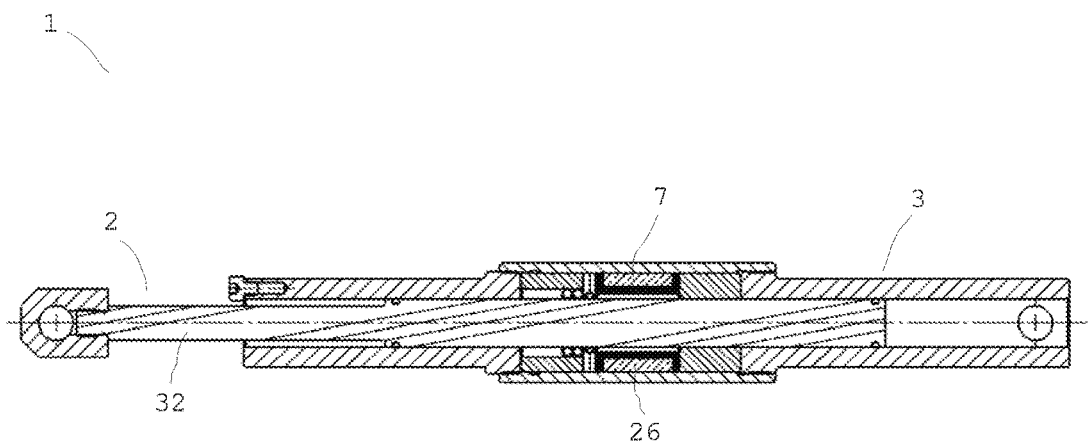
FIG. 4 shows a magnetorheological transmission device for influencing linear movements.

FIG. 4 shows a magnetorheological transmission device 1 for influencing the linear movements of two components 2 and 3 relative to one another. The magnetorheological transmission device 1 comprises a rod 32, which dips into the component 3 and is provided so it is displaceable therein relative to the component 3. The magnetorheological transmission device 1 according to FIG. 4 can be designed so that in addition to a longitudinal movement, a rotational movement of the two components 2 and 3 in relation to one another can also be permitted and can be influenced by a magnetic field.

Figure 5:
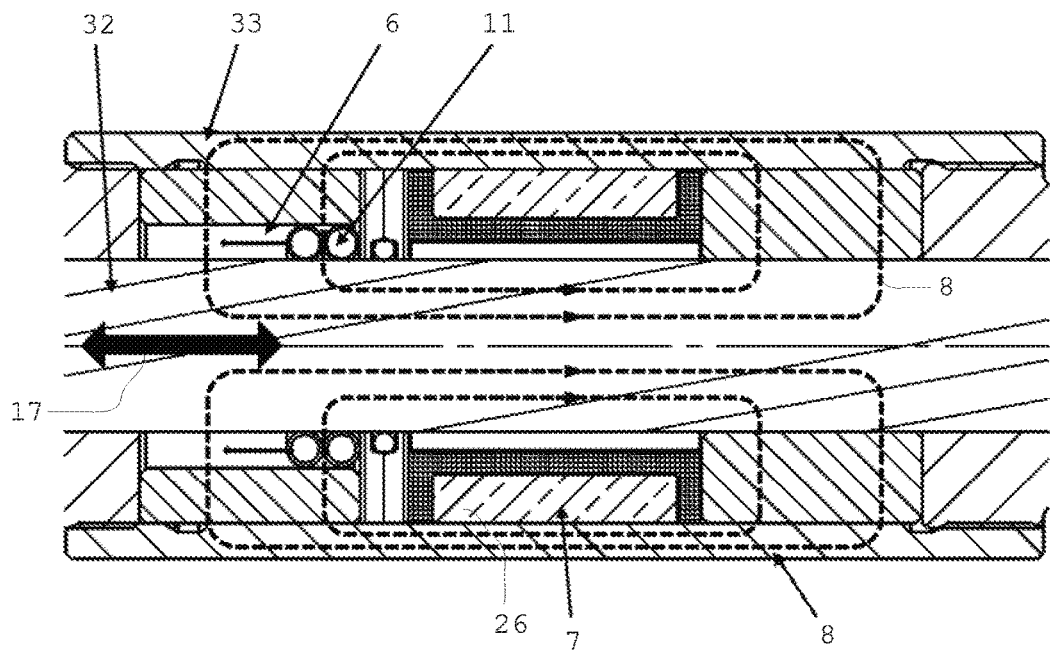
FIG. 5 shows an enlarged cross section of the device according to FIG. 4.

FIG. 5 shows an enlarged cross section of the central region of the magnetorheological transmission device 1 according to FIG. 4. The electrical coil 26 is clearly recognizable as a magnetic field generating unit 7, in order to generate a targeted magnetic field 8.

Balls are radially arranged between the rod 32 and the component 3 as rotating bodies 11, which are provided so they are movable in the axial direction relative to the rod 32 or the component 3 and move in relation to one another in the event of a relative movement of the component 2 and 3 and in particular can be set into a rotational movement. During such a rotational movement, the acute-angled regions 10 result, which in the event of activation of the magnetic field 8 result in chaining together of the particles 19 of the magnetorheological fluid 20 as the medium 6 and therefore decelerate or make more difficult or even block the relative movement of the rod 32 to the component 3. Such a magnetorheological transmission device 1 can also be used as a vibration damper or shock absorber or the like.

Figure 6:
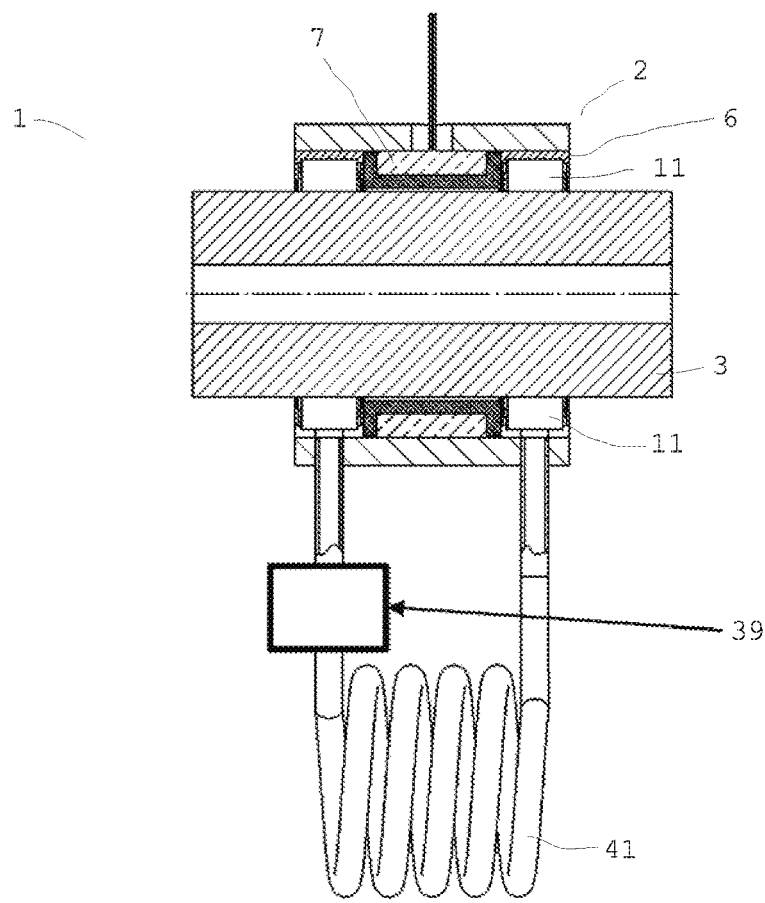
FIG. 6 shows a magnetorheological transmission device with a cooling unit.

FIG. 6 shows a magnetorheological transmission device 1 with a stationary component 2 and a rotatable component 3 embodied as a shaft, in which cylindrical rotating bodies are arranged as the rotating bodies 11 between the component 2 and the component 3 and are enclosed by a medium 6, which reacts to a magnetic field 8 of a magnetic field generating unit 7.

For example, if the magnetorheological transmission device 1 in FIG. 6 is used as a brake, the braking energy is dissipated in the medium 6. Frequent and/or strong braking can supply a large amount of energy to the medium, which can result in significant heating of the medium or fluid 6 and the rotating bodies 11. In order to dissipate the resulting heat energy, a cooling unit 41 can be provided, which can be force-activated via a pump 39, for example. The pump 39 can also be integrated in the bearing as a separate part, which utilizes the relative movement. At least a part of the rotating body and/or the components is advantageously designed so that a relative movement moves at least a part of the medium in the cooling circuit.

A further advantageous effect of a force-activated cooling unit can be continuous mixing of the liquid and the provision of sufficient MRF, wherein the cooling unit can be used as a storage container for the MRF liquid.

Figure 7:
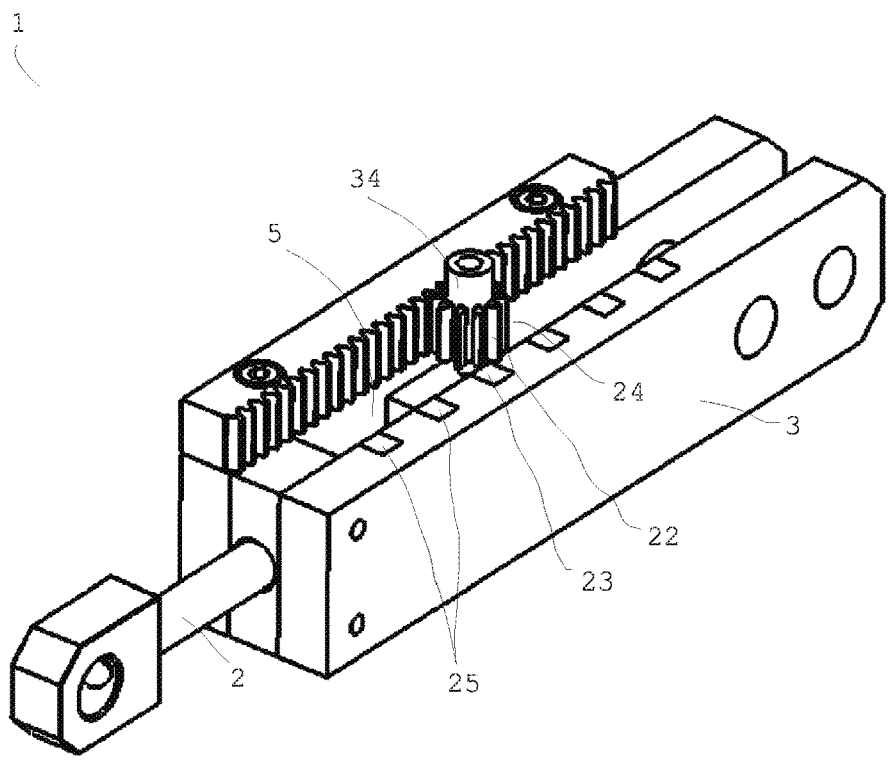
FIG. 7 shows a further magnetorheological transmission device for influencing linear movements.
Figure 8:
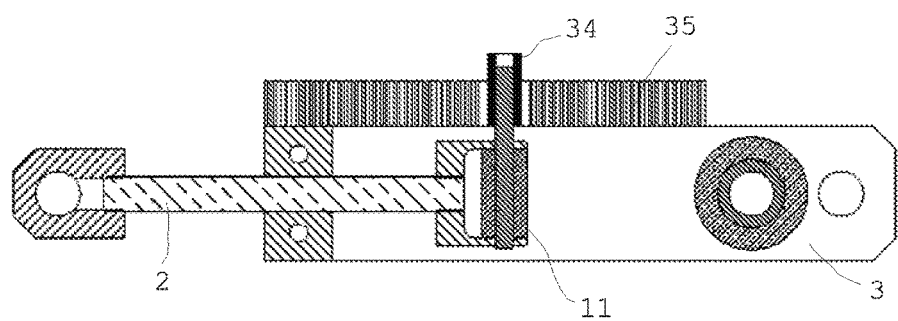
FIG. 8 shows a cross section from FIG. 7.

FIG. 8 shows a cross section of the magnetorheological transmission device 1 from FIG. 7. The component 2 has a rotatably accommodated rotating body 11, which is provided with a gear wheel 34. The gear wheel 34 meshes with a toothed rack 35 of the component 3. If the component 2 is moved relative to the component 3, it results in a rotational movement of the rotating body 11, since the gear wheel 34 of the rotating body 11 meshes with the toothed rack 34 of the component 3. If the rotating body 11 is enclosed by a medium 6, which can be influenced by a magnetic field 8, through application of an external magnetic field, a magnetorheological fluid 20 can react to the magnetic field, for example. An acute-angled region 10 having a wedge shape 16 thus respectively forms between the plates of the component 3 and the rotating body 11, which makes a further relative movement of the components 2 and 3 in relation to one another more difficult.

The gear wheel 34 and the toothed rack 35 can be dimensioned depending on the application so that the rotational velocity corresponds to the relative velocity of the components 2 and 3 in relation to one another or is increased or decreased or is strongly increased or strongly decreased, respectively.

The component 3 can also comprise only one plate, only one acute-angled region 10 having a wedge shape 16 then results.

Figure 9:
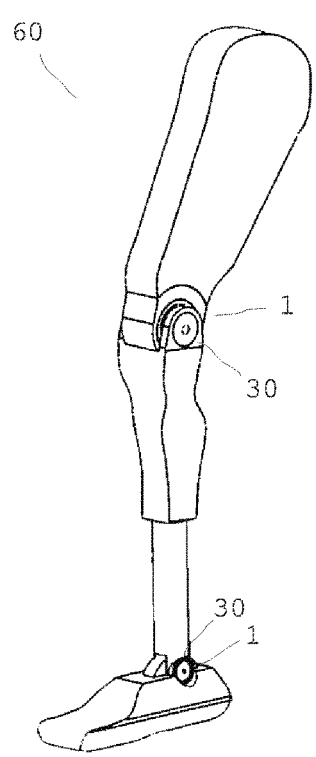
FIG. 9 shows a prosthesis with magnetorheological transmission devices according to the invention.

FIG. 9 shows a prosthesis 60, in which magnetorheological transmission devices 1 are used respectively in the knee joint and the foot joint. By activating the corresponding magnetic fields 8, a rotational movement can be damped or blocked, whereby remaining in one position is made easier and a more natural movement sequence is made possible.

Figure 10:
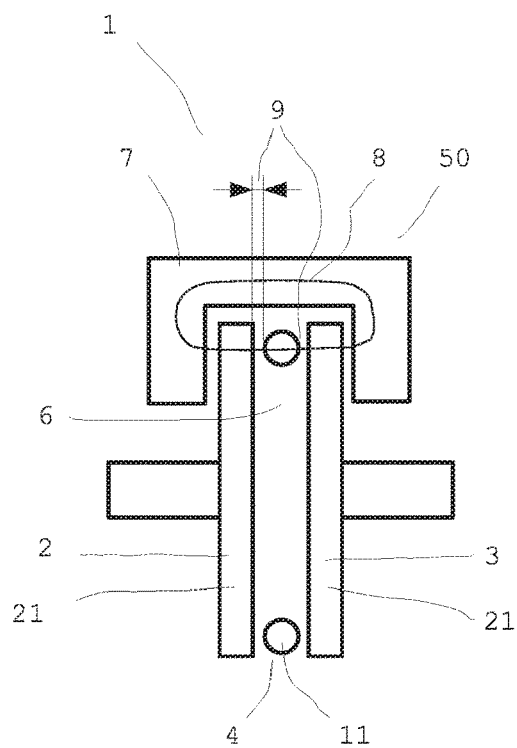
FIG. 10 shows a very schematic view of a clutch.

FIG. 10 shows a very schematic illustration of a cross section through a clutch 50. Two clutch plates 21 are provided, which are arranged at a slight distance in relation to one another. A medium 6, which is embodied as a magnetorheological fluid 20, for example, is provided between the clutch plates. Furthermore, rotating bodies 11, which are embodied here as rotating bodies 11 in the form of balls 14, are provided between the clutch plates 21. In the event of a relative movement of the clutch plates 21 in relation to one another, the rotating bodies 11 are set into rotational movement. In the event of activation of a magnetic field 8 by a magnetic field generating unit 7, this results in the formation of active acute-angled regions 10, which substantially inhibit a further relative movement of the clutch plates 21 in relation to one another.

Figure 11:
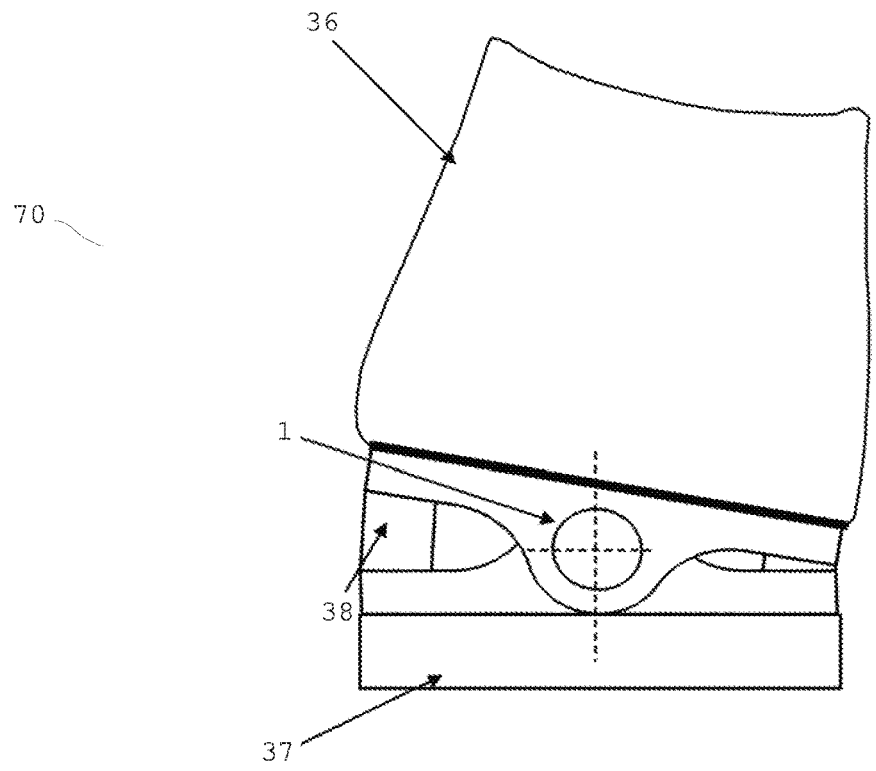
FIG. 11 shows a shoe with a magnetorheological transmission device according to the invention.

FIG. 11 shows a further exemplary embodiment of a magnetorheological transmission device 1 according to the invention, which is embodied here as a shoe 70 and is only schematically shown. The shoe 70 has an upper part 36 and a sole 37, which are connected to one another via a pivot joint having a magnetorheological transmission device 1. In order to predefine a base position, a spring unit or a foam 38 is provided, which preloads the shoe 70 in its base position. Hyperpronation or supination can be flexibly compensated for by such a shoe, in that specific angles of inclination are permitted or obstructed. Electronics, sensors, power storage unit, etc. are not shown here for better comprehensibility of the illustration. These elements can preferably be integrated in the sole 37.

Since the force on the two components can be adapted in the millisecond range so that the upper part 36 assumes an arbitrary inclination in relation to the sole 37, such a shoe 70 can be used to continuously compensate for incorrect positions of the human foot. A greater support for the inner foot region can thus result through an incline of the running shoe sole, which is advantageous in the event of hyperpronation, for example. Depending on the running speed, underlying surface, and muscle state, which is also decisively influenced by fatigue, the foot space shape adapts to the new conditions, so that the runner having a shoe 70 according to the invention assumes a good position in the running shoe. It is also conceivable that in the event of greater requested adjustment distances, the adjustment procedure is divided into multiple steps. A damping material can optionally also be integrated in the shoe. Sensors can detect the actual state and perform adaptations by means of control and/or regulating electronics. It is also possible to arrange an actuator at the end of the running shoe and not only under the running shoe or under the heel, respectively. An adjustment knob or rotating knob can practically then be arranged at the end of the running shoe.

Figure 12:
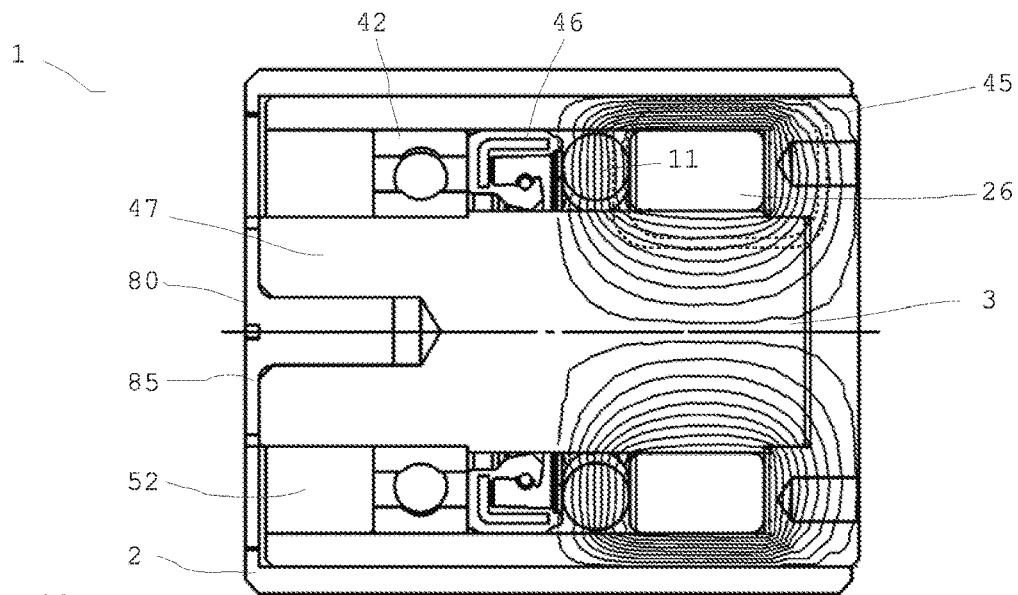
FIG. 12 shows a rotating knob with a magnetorheological transmission device according to the invention.

FIG. 12 shows an operating knob or rotating knob 80 having a magnetorheological transmission device 1 according to the invention in a schematic cross section. The housing 45 as the component 2 can be fixedly attached to a device, for example. The shaft 47 as the component 3 is connected to the rotating part 85. Both components 2 and 3 are mounted so they are rotatable in relation to one another via bearings 42. A thin gap as the free distance 9 is located between the rotating body 11 and the housing 45 and also between the rotating body 11 and the shaft 47. The space enclosing the rotating bodies 11 and optionally nearly the entire inner space can be filled with a magnetorheological fluid as the medium 6. A sealing ring 46 acts as the seal in relation to the bearing 42, which is thus protected from the particles in the magnetorheological fluid.

In the event of activation of the coil 26, a magnetic field 8 is generated, which passes through the rotating bodies 11 and otherwise runs substantially inside the housing 45 and the shaft 47 here, as shown by the field lines drawn as examples. If the magnetic field of the coil 26 is activated, a corresponding resistance is generated in the medium 6 or the MR fluid, so that a corresponding resistance is perceptible during rotation of the rotating part 85. A time-pulsed or pulsating operation is also possible, for example, due to which a pulsing resistance and therefore a pattern is perceptible during the rotation.

The respective current angular position can be detected via a rotary encoder 52. Arbitrary haptic signals can thus be output depending on the activation according to the position, rotational angle, angular velocity, etc. The rotary encoder 52 can also be supplemented with a torque sensor.

Figure 12B:
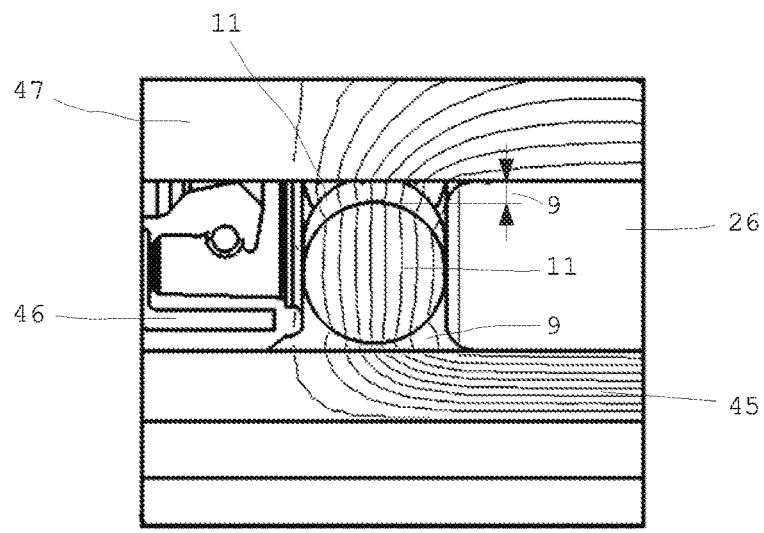
FIG. 12B is a diagrammatic view of the magnetic field lines through the rotating knob shaft according to the invention.

FIG. 12*b* shows a schematic enlarged detail from FIG. 12, in which one rotating body 11 is entirely visible and one rotating body 11 arranged behind it is only partially visible, since it is partially concealed by the front rotating body 11 and is slightly concealed by the shaft 47. The gap or free distance 9 above and below the rotating body 11 is clearly recognizable. The free distances can be equal on the radial inside and radial outside, but do not have to be. The free distance 9 corresponds in bearing terminology to the running profile. In the case of a bearing, twice the running profile corresponds to the bearing clearance.

FIG. 12*b* also shows that separate running surfaces are not provided on the shaft 47 and also in the housing 45 as the components 2, 3. The transmission of a clutch or brake torque occurs via the rotating bodies and the amplifying wedge effect of the MRF.

Figure 13:
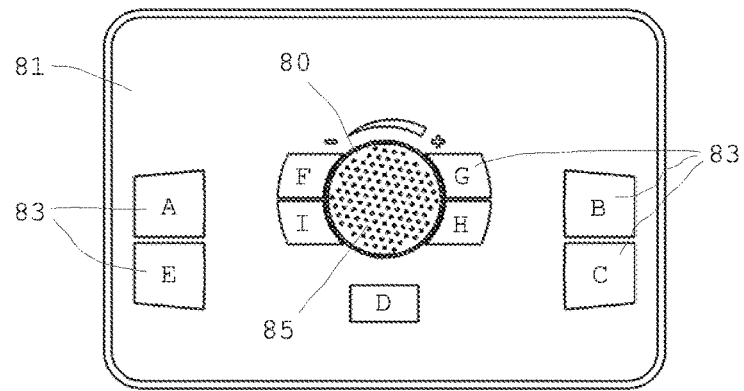
FIG. 13 shows the rotating knob from FIG. 12 with a display.

FIG. 13 shows a rotating knob 80, which is arranged on a display screen or on a display 81. Further operating elements or buttons 83 can also be provided on the display 81. The display 81 can also be implemented so it is touch sensitive as a touchscreen and can display knobs or buttons 83, for example. For example, it is possible that the buttons 83 are shown depending on the program and/or selection or are activated to make individual operation easier for the user.

Two-dimensional haptic knobs or rotating knobs 80 can also be produced with an additional MRF shear mode.

An MRF haptic knob can be embodied very compactly for actuating units in SLR cameras and other photographic apparatuses, as well as in games consoles and other handheld computers. Such compact MRF coupling units are well suitable for cameras and other outdoor applications because of the small space requirement and the low power consumption in the range of milliwatts or less. The pattern is settable depending on the situation.

Three-dimensional movement elements with variable haptics and robust and precise mounting are fundamentally difficult to produce and are therefore not cost-effective. The combination, for example, of an arrangement of the rotating bodies which is capable of pendulum movements with a magnetorheological fluid is very cost-effectively producible, in contrast.

A four-dimensional rotating knob, which can be displaced in three directions and can additionally also be rotated, for example, can also be provided.

The combination of a 3-D knob with a longitudinal adjustment of an MRF wedge thus results in a 4-D actuating element. All four movement directions can be influenced or varied using a field generating unit.

The use of such haptic knobs is also possible on touch-sensitive displays such as touch display screens in mobile telephones, PDAs, smart phones, portable and stationary computers, and display screens, games consoles, tablet PCs, laptops, etc. For this purpose, at least one haptic element in the form of a rotating knob is provided therein, for example.

Such a haptic element 1 can also be embodied as foldable/pivotable or displaceable and can be displaced from an idle position on the edge into a position over the display screen, for example. As soon as the haptic element is over the display screen, the display on the display screen can change, i.e., a menu appears under or around the knob.

Instead of a kinematic and parallelogram-like pivot mechanism, for example, an elastic/deformable element can also be used, which can consist of a flexible and semirigid arm made of coiled metal tubing in the form of a gooseneck, for example. One advantage is that the user does not always have to grasp the display screen, which reduces the soiling. In addition, the adjustment and the zooming, for example, go more rapidly: grasping in the display screen with one finger and moving the rotating regulator with other fingers can trigger a zoom procedure, for example. This is also true for the volume, writing with uppercase and lowercase letters, or the selection of special buttons or a second level during typing.

The user can thus also press with one finger on a separate menu bar, in order to search for the type of the desired actuation. He then performs the desired action using the rotating regulator. The pattern of the rotating regulator then adapts automatically, thus, for example, "on"-"off" or a volume regulation with a pattern possibly having a dynamic stop. If the display screen is rotated during the actuation (touch display screen) (for example, as in the case of mobile telephones or handheld computers—90° from portrait format to landscape format), the pattern adapts automatically, i.e., it also rotates. For example, if the setting range were from six o'clock to 12 o'clock when it is held by the edge, this would change from 12 o'clock to six o'clock upon rotation by 90° clockwise without adaptation. This is also true if the display screen is installed in the knob itself. Such a haptic element can be haptic in all or individual directions (only rotate, rotate and press; joystick, etc.). The haptics adjust themselves depending on the selected action.

One advantage can also result upon the selection of a list such as a telephone book list, for example, since such entries are often too small for "targeting" for large fingers.

Advantages also result in the dark or for people with spectacles who are not currently wearing them. Feedback is received via the haptic rotating regulator and the user knows what he is doing when it is currently dark, for example.

Figure 13B:
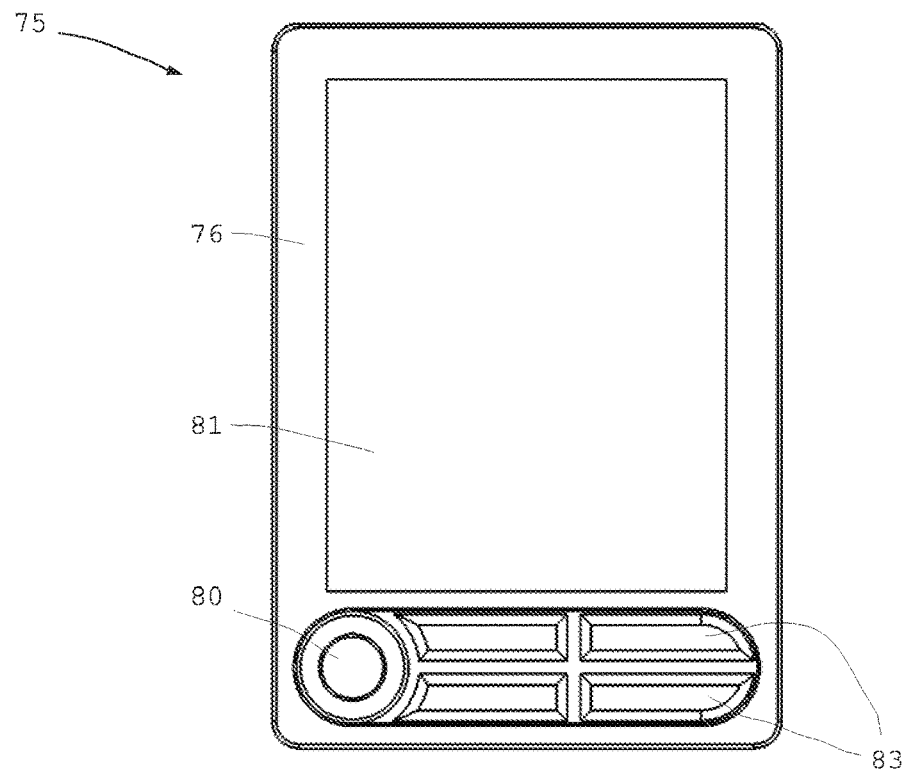
FIG. 13B shows a plan view of a portable computer with an operating knob.

In FIG. 13B, a plan view of a portable computer 75 with a housing 76 is shown. A display 81 and at least one operating knob 80 are provided on the housing 76. The screen or the display 81 is of a touch-sensitive embodiment and reacts for example to touching with a finger and/or operating with a pen. In particular, the portable computer 75 and the display 81 are designed to be controlled by gestures.

The portable computer 75 can be operated by appropriate actions of touching with a finger and/or using swiping gestures. Programs can be started and operated and can also be ended again.

Figure 13C:
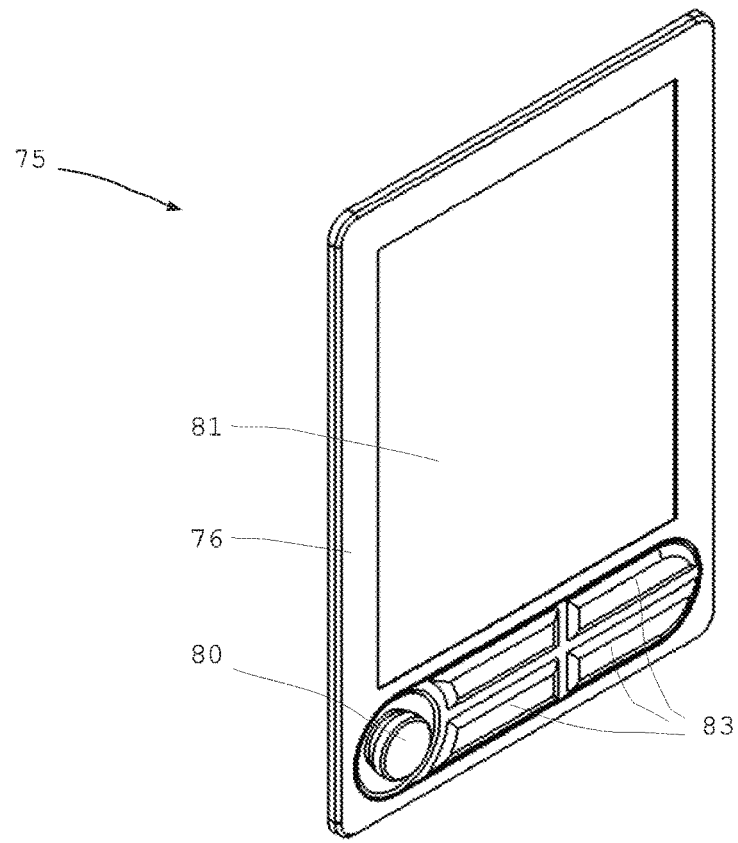
FIG. 13C is a perspective view of the portable computer according to FIG. 13B.

FIG. 13C shows a perspective view of the portable computer 75 according to FIG. 13B. The operating knob 80 protrudes out a little here, so that the rotatable operating knob 80 can be conveniently gripped and turned. In addition, a button 83 or a number of (mechanical) operating buttons may be provided, such as for example separate buttons for "back" or "home" or "menu" and so on.

It is possible and preferred to use an operating knob 80 that is mechanically and/or electrically constructed in the way shown in one of FIG. 12, 12B or 13. The haptic knob or the operating knob 80 is preferably rotatable by more than 360° and in the switched-off state is in particular continuously rotatable. The haptic operating knob 80 may be advantageously used for operating the portable computer 75. Similarly, a stationary computer or a stationary display device and/or operating device with such an operating knob 80 may be used.

The haptic knob or the operating knob 80 may also be embodied as foldable or pivotable or displaceable. It may for example be displaced from the idle position into a position over the display screen. As soon as the haptic knob or the operating knob 80 is over the display screen, the display on the display screen changes and, for example, a menu may appear in the proximity of the knob.

Figure 14:
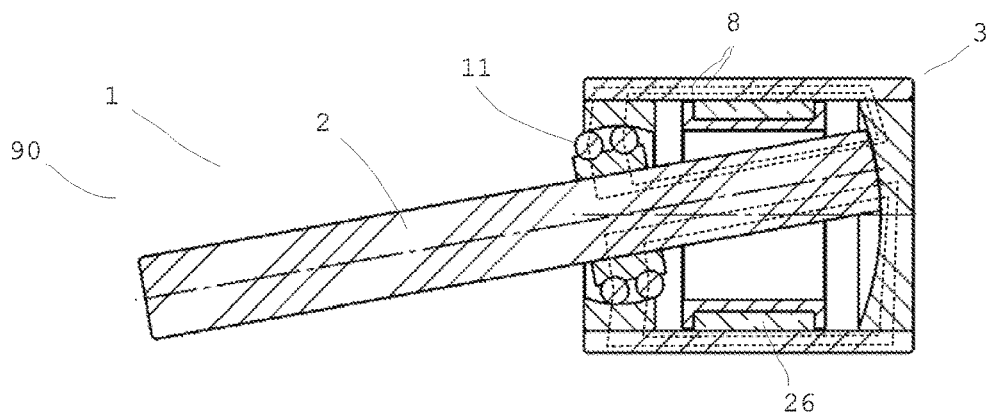
FIG. 14 shows a joystick with a magnetorheological transmission device according to the invention.

FIG. 14 shows such a 3-D knob as a joystick 90, which is provided so it is pivotable in various directions. A haptic pattern can be implemented by sensor-controlled or time-controlled activation of the coil 26. Magnetic field lines 8 are shown as examples. Very low forces occur in this case, whereby the MRF particles are not damaged by high surface pressures.

Figure 15:
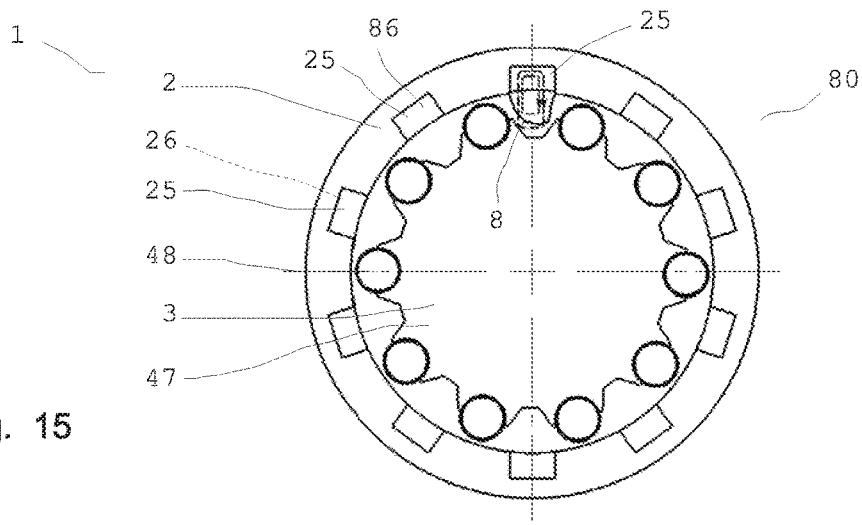
FIG. 15 shows a further rotating knob in a schematic front view.

FIG. 15 shows a schematic view of a rotating knob 80 as a magnetorheological transmission device 1, which has an outer component 2 and an inner component 3. An MRF is located in a gap 86 between the two components 2 and 3. Protrusions 49, which act as radial projections, protrude from the component 3 embodied as the shaft 47. In addition, permanent magnets 25 are provided at predetermined angular intervals as magnetic field generating units or magnet units or projections on the component 2. The magnetic fields of the permanent magnets 25 result in a local cluster formation in the medium 6. The effect is thus amplified, so that substantial torques can be absorbed. The arrangement of the magnet units 87 results in a perceptible pattern during the rotation of the rotating knob 80. In FIG. 15, the protrusions are partially formed by separate rotating bodies 11, which are arranged in corresponding recesses 88 of the protrusions 49, and can preferably rotate therein.

Figure 16:
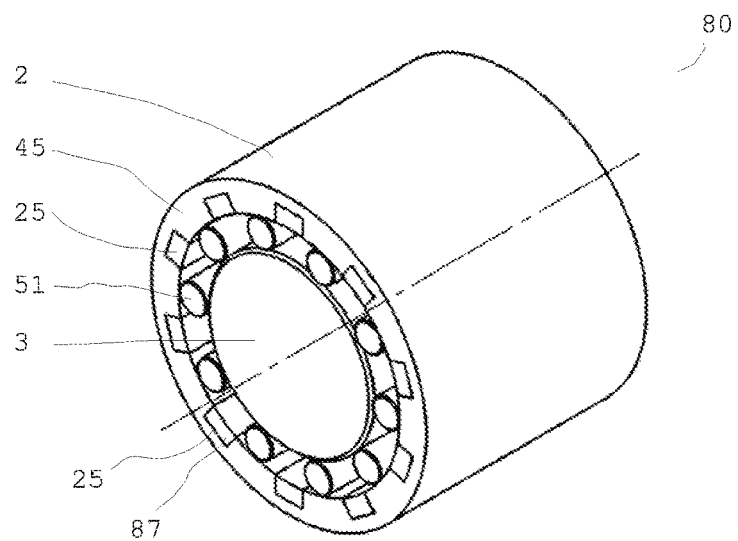
FIG. 16 shows another rotating knob in a schematic perspective view.

FIG. 16 shows a rotating knob 80, in which rotating bodies 11 or rolling bodies 51 are provided between the inner component 3 and the outer component 2.

It is possible that the magnetic field goes radially through the gap and/or the rotating bodies 51. It is also possible that the magnetic field goes axially through the gap and/or the rotating bodies 51, for example, axially in on one side and back out on the other side. Furthermore, a combination of the above-mentioned alternatives is also possible.

In concrete embodiments, the cage can also be provided with a friction-increasing layer or can be manufactured from a special material, whereby the torque difference between "turned on" and "turned off" increases. Instead of a rotational mode, a linear mode of operation can also be possible.

Ball recirculation bushes or linear bearings with cage or linear ball bearings can also be used to achieve sustainable support.

The overall construction is producible very simply and cost-effectively, since such rotating bodies are mass-produced articles.

In all cases, eddy current effects can be taken into consideration in the case of rapidly rotating rotating bodies.

It is possible to produce one or both components at least partially and/or individual ones or all of the rotating bodies 11 or 51 from a magnetorheological MR plastic or magnetorheological elastomeric material, which changes its shape depending on the field strength and thus clamps the rotating bodies. Such a system can manage completely without a seal.

One embodiment has MRF bound in plastic such as foam or a sponge. A solid lubricant, thus, e.g., lithium, graphite, or MoS2 or the like could be mixed with carbonyl iron powder as the MR powder.

Conventional roller bearings or plain bearings can be used for mounting components 2, 3, which are rotatable in relation to one another. In specific cases, for example, at very low loads, separate bearings can also be omitted.

Figure 17:
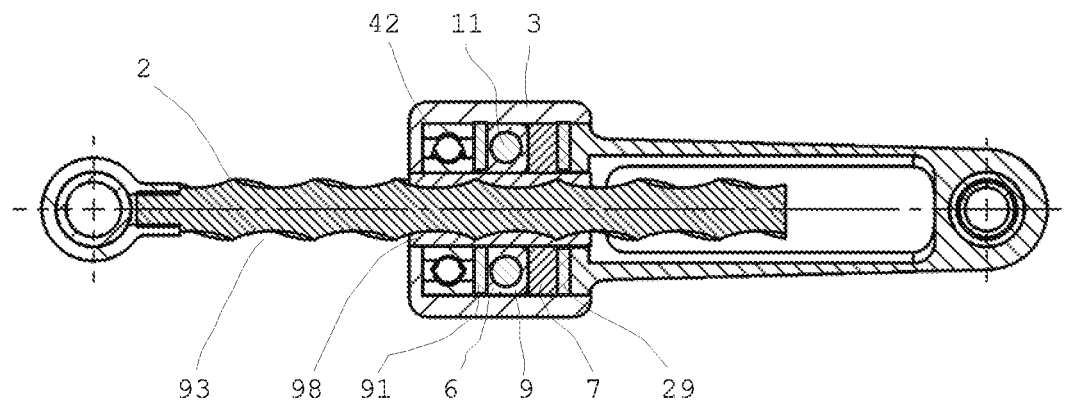
FIG. 17 shows a further magnetorheological transmission device in a sectional view.

FIG. 17 shows an embodiment of a magnetorheological transmission device 1, in which a linear movement such as a stroke or the like via a spindle, for example, a ball spindle or a simple spindle, is converted into a rotational movement. The one component 2 is embodied as a threaded spindle 93 and is moved linearly. A spindle nut 98 is seated thereon. A linear movement is converted into a rotational movement. Bearings 42 can be provided for the mounting, which are then sealed via a seal 91.

The rotating bodies 11 are arranged in a gap 5, which is filled with MRF. The gap can be subjected to a magnetic field of the magnetic field generating unit 7, whereby the relative movement of the components 2 and 3 is damped and the stroke movement is in turn influenced. Use is possible in different applications, for example, in sporting devices or washing machines as a damper.

Optionally, the magnetorheological transmission device 1 as the MRF brake can also be expanded with a rotary encoder 29. The detection of a rotational movement is more cost-effective and simpler to implement than the detection of a longitudinal movement. This is also true for the sealing. In addition to or instead of the rotary encoder 29, a torque sensor can also be used.

In all embodiments, one or at least one permanent magnet can be provided, which is adjustable by motor or by hand. The use of a displaceable shield is also possible. In all cases, mechanical setting of the brake action and therefore the wedge effect is possible. This can be used, for example, to compensate for physical variables such as temperature, pressure, speed, or the like. The actuation can be performed directly or via a Bowden cable, for example. The adjustment can be continuous.

Figure 18:
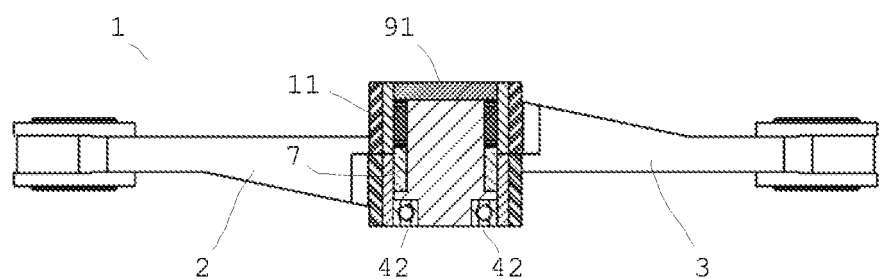
FIG. 18 shows a toggle lever as a magnetorheological transmission device in a sectional view.
Figure 19:
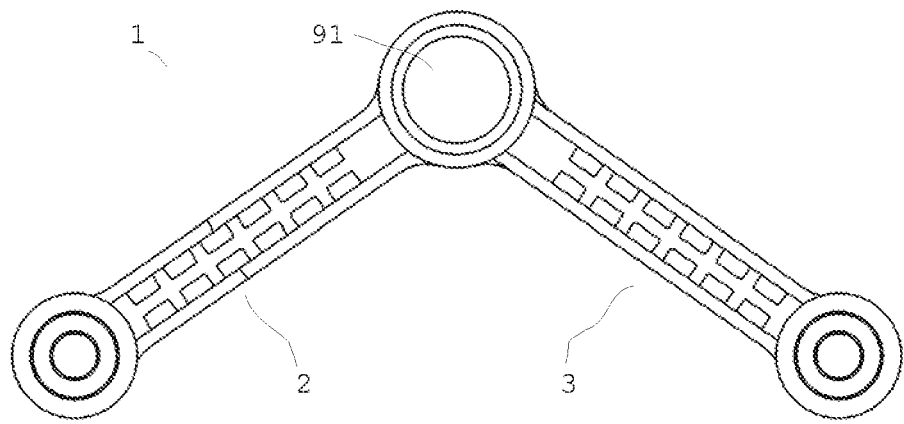
FIG. 19 shows the toggle lever from FIG. 18 in a side view.

FIGS. 18 and 19 show an MRF transmission device 1 in a toggle lever in two different views.

The toggle lever has two arms, which form the components 2 and 3, which are arranged so they are rotatable in relation to one another here. Bearings 42 can be provided for the load-bearing support. A magnetic field generating unit 7 is used to generate a magnetic field in the gap, in which an MRF and rotating bodies 11 are provided. A very high brake or clutch torque can optionally be built up by the free distance 9, which is sufficiently large, but not excessively large. A seal 91 forms the seal to the outside. The MRF transmission device 1 can also be supplemented with a rotary encoder and/or a torque sensor and/or other sensors.

Such magnetorheological transmission devices can be used for fittings in furniture. For example, as a linear unit for drawer guides, etc. Sufficient guiding is performed by the rotating bodies, while the pullout force is simultaneously variable.

In general, magnetorheological transmission devices 1 with wedge effect can be used as a variable and settable brake in kitchens and in other furniture. The pivoting, for example, the opening of doors or flaps in furniture can be restricted to specific ranges, while rapid opening is possible.

The setting can be performed via pivotable permanent magnets or electrically or via a lever or rotating lever, for example.

Figure 20:
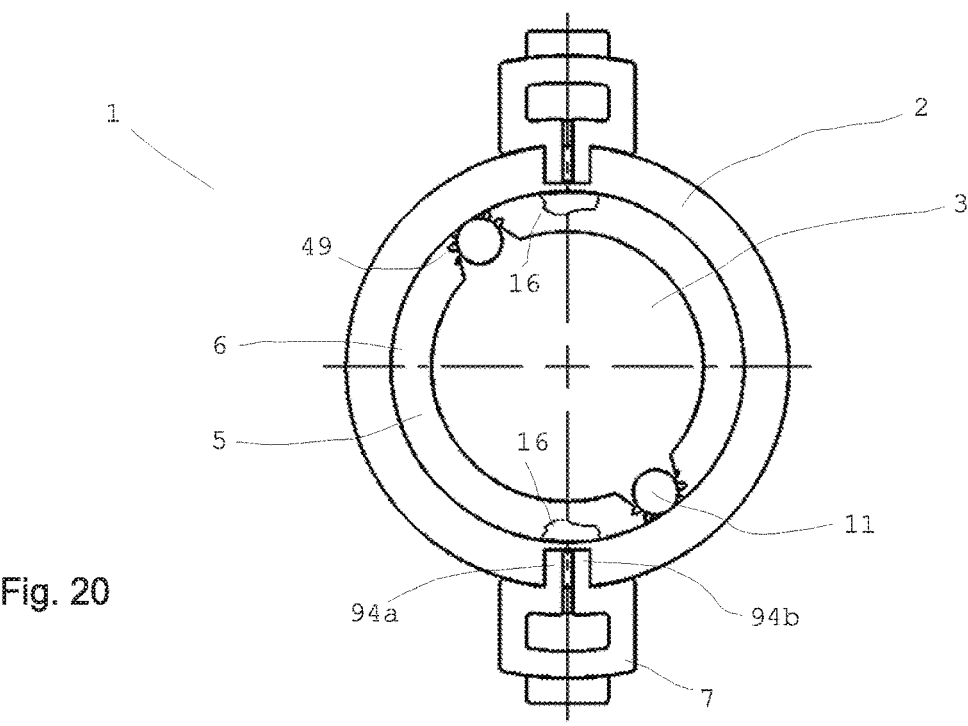
FIG. 20 shows still another magnetorheological transmission device in a front view.
Figure 21:
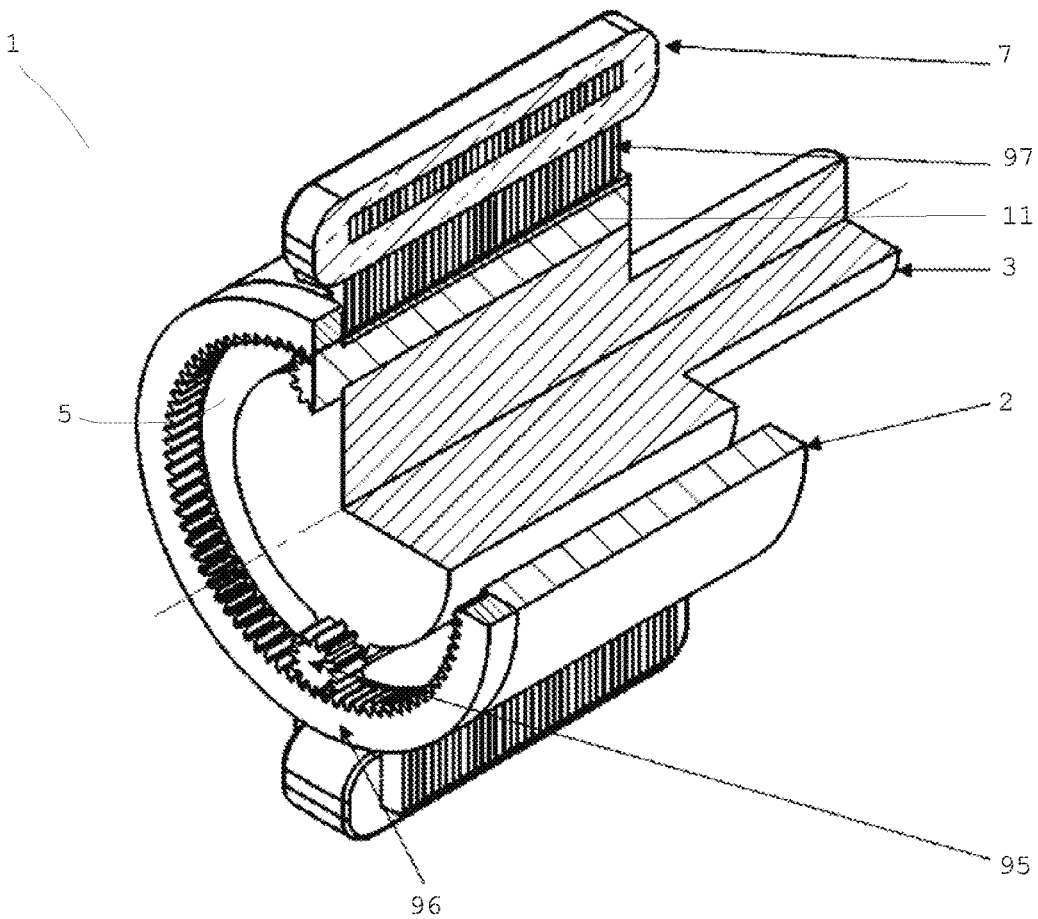
FIG. 21 shows the magnetorheological transmission device in a sectional view.

FIG. 20 shows an MRF transmission device 1 in a very schematic front view and FIG. 21 shows the transmission device 1 from FIG. 20 in a very schematic partial cross section.

An inner shaft 3 here is arranged so it is rotatable in an outer hollow shaft as the component 2. The outer hollow shaft 2 can be embodied as stationary. Two electromagnets each having a plate packet 97 are arranged on the sleeve 2 here as magnetic field generating units 7. Three or more electromagnets can also be provided. It is also possible that only one magnet is provided. Permanent magnets can be at least partially used instead of electromagnets.

A gap 5, which is filled with an MRF, is provided between the components 2 and 3. In the gap as the channel 5, two rotating bodies 11 are arranged here, which are embodied here as substantially cylindrical rotating bodies. At one end, the cylindrical rotating bodies 11 can be provided with pinions 95, which are force-guided in gear teeth 96, so that a continuous rotational movement of the rotating bodies 11 is ensured. The region of the gear teeth 96 can be substantially free of field and MRF. The coupling predominantly occurs here via the wedge forming in the gap 5. The transmission device can be implemented with various gear teeth or transmission ratios, or also without them, for the forced rotation of the rotating bodies 11.

The magnetic field generating units 7 shown in FIG. 20 each have a north pole 94a and a south pole 94b, which border the channel 5 with the MRF located therein at a small distance from one another. The magnetic field lines run through the two poles 94a and 94b into the ring gap as the channel 5 and form clusters of solidifying MRF therein when the field is applied. The rotating bodies, which are embodied as cylindrical in the region of the ring gap, run on the MRF structures during the forced rotational movement. The wedge effect then resulting and the acute-angled region at the rotating bodies result in a very strong braking torque.

Figure 22:
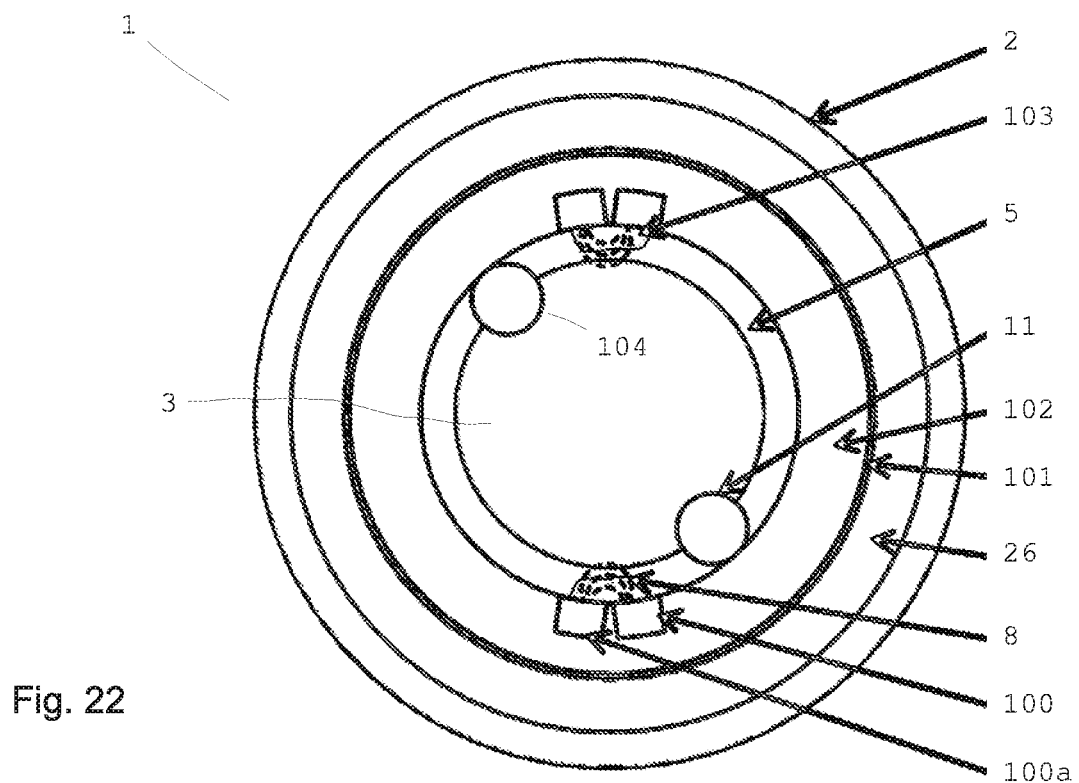
FIG. 22 shows still a further magnetorheological transmission device in a sectional view.
Figure 23:
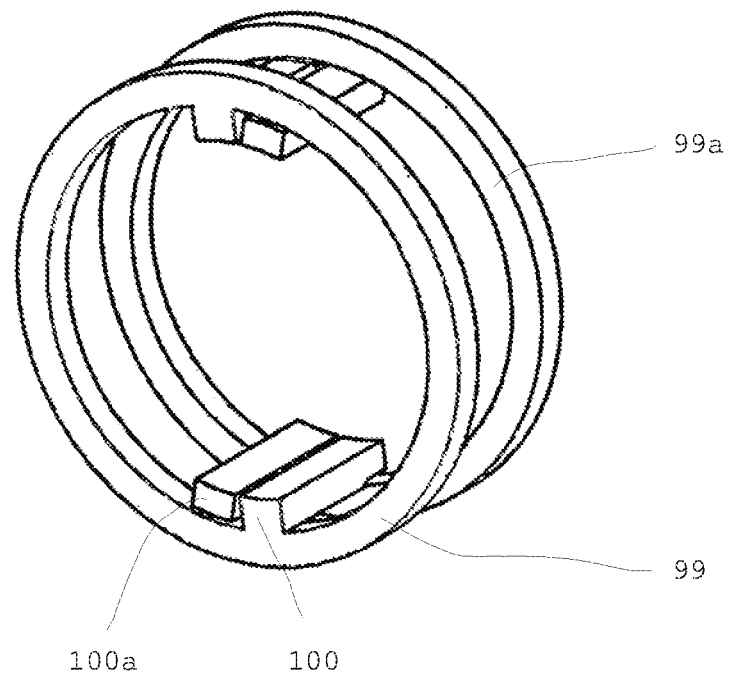
FIG. 23 shows the pole plates of the magnetorheological transmission device from FIG. 22.

Such a magnetorheological transmission device 1 as a wedge clutch according to FIG. 20 can also have a coil fastened in a nonrotating housing, which optionally generates a magnetic field, in an alteration according to FIG. 22. The magnetic field is conducted via pole plates 99 and 99a and is closed via fingers 100 and 100a, which are fastened axially on the pole plates 99 and 99a. The MRF is solidified to form clusters 103 in the MRF channel 5 or gap between the fingers 100 and 100a of the pole plates 99 and 99a. The pole plates 99 and 99a rotate with the drive shaft 2. If the solidified MRF regions 103 meet the rotating bodies 11 arranged in the semicircular recesses 104, which rotating bodies are fastened on the output shaft 3, these rotating bodies are briefly entrained by the magnetic field.

The coils can be provided as stationary by transmitting the field 8 radially from the outside via the air gap 101 into the pole plates 99 and 99a. Transmitting the power supply via slip rings is not necessary. The magnetic flux is introduced via the pole plates 99 and 99a and their pole fingers 100 and 100a into the channel 5, where the field lines close and result in the formation of the clusters 103, which interact in a wedge shape with the rotating bodies 11.

The pole plates 99 and 99a are held in a ring, which comprises plastic here, and which is separated via an air gap 101 from the externally rotating component 2 or shaft.

All components are preferably ferromagnetic, except for the part, which is embodied in particular as a plastic part, between the pole plates 99 and 99a and the drive shaft and output shaft 2 and 3.

The two "finger pairs" (MRF clusters) can optionally be activated individually and independently of one another.

In all cases, it is also possible to install magnetorheological transmission devices 1 with wedge effect in a wheel hub of a vehicle, for example, a bicycle, in order to brake, for example. The required electrical power can be acquired as current directly from the installed dynamo, which is connected parallel thereto in particular. Power reclamation can occur via the dynamo. In the event of (full) braking, the magnetorheological transmission device 1 can be used as an MRF brake. The system is coordinated. Since such an MRF brake functions solely electrically and reacts rapidly, the use is well possible. Corresponding running surfaces for the rotating bodies are provided. A majority could thus be braked via a wheel hub dynamo. For the actuation on the handlebars, only a power cable in conjunction with a potentiometer, for example, is required or the transmission is performed wirelessly.

The use as a brake in fitness devices or as a clutch or brake on rowing machines is also possible. The principle can also be taken as a wedge clutch for engaging assemblies and in particular secondary assemblies in the case of motor vehicles. If necessary, two MRF clusters can be provided relatively close to one another, so that the system does not open immediately in the event of a rotational direction change.

In the event of overload, such a clutch opens automatically. No slip rings are optionally required for the power transmission. It can occur via remanence, for example.

If in such an MRF wedge clutch the rotating body 11 still jumps over the MRF wedge or MRF cluster during the first engagement attempt, the leading part is thus accelerated and the engagement procedure is made easier during the second attempt. The use as a free wheel is also possible, by rapidly detecting the rotational direction and turning off the field if another rotational direction is recognized.

The use in a clutch in milling machines is also possible, wherein, for example, disengagement occurs if the emergency shutdown switch is pressed during the running of the machine. It is also possible to suddenly disconnect the clutch in the event of overload. Normal (MRF) clutches do not reduce the torque suddenly.

In all cases and designs, the wedge and/or the magnetic field can also be generated on the inner ring and not only on the outer ring.

The rotating bodies 11 and cages can be embodied as entirely or partially ferromagnetic and paramagnetic or diamagnetic. A completely spherical embodiment and an embodiment in which all parts consist of the same material are also possible. It is also possible that some rotating bodies are ferromagnetic and consist of steel, for example, while others consist of plastic. The use of rotating bodies and balls with different diameters is also possible.

The magnetorheological transmission device 1 according to the invention can preferably also be used for speed recognition and in particular speed regulation.

The torque can be set depending on the speed via pulse width modulation (PWM). Large axial and radial forces can be generated via an inclined spreading mandrel. The particles can be round, rod-shaped, or have any other shape.

It is also possible to use magnetorheological elastomeric materials. For example, at least one surface can also be a magnetorheological elastomeric material. Fundamentally, a component can be provided with a magnetorheological elastomeric material. It is also possible to coat at least one rotating body 11 and/or at least one of the components 2, 3 with a magnetorheological elastomeric material.

The magnetorheological transmission device 1 can also be embodied as a valve, wherein one rotating body 11 or multiple rotating bodies 11 block the channel.

A magnetorheological transmission device can also be provided for the use of a magnetorheological fluid, which is a product of BASF, in particular the product "Basonetic".

The rheological liquid can consist of greatly varying ingredients, which can be, individually or in combination: iron, carbon steel, NdFeB (neodymium), Alnico, samarium, cobalt, silicon, carbon fibers, stainless steel, polymers, soda lime glass, soda glass, ceramic, and nonmagnetic metals and the like. Dimorphic magnetorheological fluids with nanotubes and/or nanowires are also possible.

The carrier liquid can consist in particular of the following ingredients or a combination thereof: oils and preferably synthetic or non-synthetic oils, hydraulic oil, glycol, water, greases, and the like.

LIST OF REFERENCE NUMERALS 1 device
2, 3 component
4 separate part
5 channel
6 medium
7 magnetic field generating unit
8 field
9 free distance
10 acute-angled region
11 rotating body
12 rotational axis
13 rotating body
14 ball
15 cylinder
16 wedge shape
17 direction of the relative movement
18 direction of the relative movement
19 magnetic particles
20 fluid
21 plate
22 outer side
23 projection
24 gear teeth
25 permanent magnet
26 coil
27 control unit
28 energy store
29 sensor
30 bearing
31 stationary component
32 rod
33 outer tube
34 gear wheel
35 toothed rack
36 upper part of shoe
37 sole
38 foam
39 pump
40 brake
41 cooling unit
42 bearing
45 housing
46 sealing ring
47 shaft
49 protrusion
50 clutch
51 rolling body
52 rotary encoder
60 prosthesis
70 shoe
75 computer
76 housing
80 operating knob
81 display
82 touchscreen
83 button
84 loudspeaker
85 rotating part
86 gap
87 magnet unit
88 recess
90 joystick
91 seal
92 running profile
93 threaded spindle
94$a$ north pole
94$b$ south pole
95 pinion
96 gear teeth
97 plate packet
98 spindle nut
99 pole plate
99$a$ pole plate
100 finger
100$a$ finger
101 air gap
102 plastic ring
103 cluster
104 receptacle

The invention claimed is:

1. A haptic interface for operating an electronic device, comprising:

a rotary element to be manually activated, said rotary element being mounted to be freely rotatable in a non-energized state of the haptic interface;

an integrated rotary encoder associated with said rotary element and disposed to interpret a rotation of said rotary element upon manual activation thereof; and a control unit, connected to said integrated rotary encoder, and a touch display, connected to said control unit, for displaying a given selected menu with a plurality of menu items for control of the electronic device and enabling user input for choosing a respective one of said menu items;

a transmission device coupling said rotary element to the electronic device to be operated via the haptic interface with a given variable coupling intensity;

said transmission device having an outer component and an inner component rotatably mounted relative to one another, wherein one of said outer and inner components is connected to said rotary element and the other of said outer and inner components is connected to the electronic device;

a field generating unit controlled by said control unit for generating an electromagnetic field in order to influence, by way of an intensity of the electromagnetic field, the coupling intensity between said rotary element and the electronic device, and the coupling intensity defining a haptic behavior of said haptic element and a resistance to a movement of said rotary element under control of said control unit in dependence on a currently selected menu.

2. The haptic interface according to claim 1, which comprises a settable end stop for said rotary element and wherein said end stop is set in dependence on the currently selected menu.

3. The haptic interface according to claim 1, which further comprises a loudspeaker configured to provide audible feedback upon the manual activation of said rotary element and in accordance with the currently selected menu.

4. The haptic interface according to claim 1, wherein the electronic device is a computing device selected from the group consisting of a mobile telephone, a PDA, a smart phone, a portable computer, a stationary computer, a display screen, a game console, a tablet computer and a laptop computer, and said rotary element is a rotary knob associated with said computing device and configured as an input device for said computing device.

5. The haptic interface according to claim 1, which further comprises a magnetorheological transmission device coupling said rotary element to said rotary encoder and to the electronic device being a smart device to be operated via the haptic interface with a given variable coupling intensity;

said outer component and said inner component are disposed to form a channel therebetween;

an amount of magnetorheological medium disposed in said channel for influencing the coupling intensity between said rotary element and the smart device;

said field generating unit being a magnetic field generating unit configured for generating a magnetic field in said channel in order to influence a flow characteristic of said magnetorheological medium in said channel by way of the magnetic field;

wherein an intensity of the magnetic field generated by said magnetic field generating unit defines the haptic behavior of said haptic element and the resistance to the movement of said rotary element.

6. The haptic interface according to claim 5, wherein said magnetic field generating unit is configured to generate haptic feedback via variable detent torques with respect to a strength, a rotational angle, or an end stop for a rotation of said rotary element.

7. The haptic interface according to claim 1, wherein said rotary element is a rotating knob housing a control command transmission unit mounted within said knob for wireless transmission of control commands.

8. The haptic interface according to claim 7, wherein said control command transmission unit is a Bluetooth unit.

9. The haptic interface according to claim 8, which further comprises an energy supply disposed in said knob for powering said Bluetooth unit.

10. The haptic interface according to claim 1, wherein said rotary element is a haptic knob configured to be manually rotated and to be manually depressed for selective menu activation.

11. A method of adjusting a smart device, the method comprising:

providing a rotating element for manual activation, the rotating element being freely rotatably mounted, and a touch display for manual input to the smart device;

encoding a rotation of the rotating element upon a manual activation thereof with a rotary encoder;

providing a magnetorheological transmission device coupling the rotary element to the rotary encoder and a smart device to be operated via the hapitc interface with a given variable coupling intensity, the transmission device having an outer component and an inner component rotatably mounted relative to one another and forming a channel therebetween;

wherein one of the outer and inner components is connected to the rotary element and the other of the outer and inner components is connected to the smart device;

a magnetic field generating unit configured for generating a magnetic field in the channel in order to influence a flow characteristic of a magnetorheological medium in the channel by way of the magnetic field;

wherein an intensity of the magnetic field generated by the magnetic field generating unit defines a haptic behavior of the haptic element and a resistance to the rotation of the rotary element;

controlling an input of the smart device in accordance with the manual activation of the rotating element and providing haptic feedback via the rotating element in accordance with a currently displayed menu on the touch display of the smart device or in dependence on a selected action; and controlling a further input of the smart device by manually touching a respective menu item displayed on the touch display.

12. The method according to claim 11, wherein the haptic feedback via the rotating element is a resistance against a rotation thereof and wherein the resistance is dynamically variable.

13. The method according to claim 12, wherein the dynamically variable resistance is provided for haptic feedback to a user controlling the smart device and for enabling actuation of the rotating element without visual inspection.

14. A smart device with a haptic interface, comprising:

a rotary element to be manually activated, said rotary element being mounted to be freely rotatable in a non-energized state of the haptic interface;

an integrated rotary encoder associated with said rotary element and disposed to interpret a rotation of said rotary element upon manual activation thereof;

a touch display for displaying menus and enabling a user to select given menu items from a respectively selected menu by touching the touch display;

a magnetorheological transmission device coupling said rotary element to said rotary encoder and a smart device to be operated via the hapitc interface with a given variable coupling intensity;

said transmission device having an outer component and an inner component rotatably mounted relative to one another and forming a channel therebetween;

wherein one of said outer and inner components is connected to said rotary element and the other of said outer and inner components is connected to the smart device;

an amount of magnetorheological medium disposed in said channel for influencing the coupling intensity between said rotary element and the smart device;

a magnetic field generating unit configured for generating a magnetic field in said channel in order to influence a flow characteristic of said magnetorheological medium in said channel by way of the magnetic field;

wherein an intensity of the magnetic field generated by said magnetic field generating unit defines a haptic behavior of said haptic element and a resistance to the movement of said rotary element;
a control unit, connected to said integrated rotary encoder and to said touch display;
wherein said control unit is configured to change at least one property of the haptic interface depending on a currently selected action for providing responsive feedback through the rotary element.

15. A haptic interface for operating a smart device, the smart device having a display for displaying selected menu items, the haptic interface comprising:
a rotary element to be manually activated;
an integrated rotary encoder connected to the smart device, said rotary encoder being associated with said rotary element and disposed to interpret a rotation of said rotary element upon manual activation thereof;
a magnetorheological transmission device coupling said rotary element to the smart device with a given variable coupling intensity;
said magnetorheological transmission device having an outer component and an inner component rotatably mounted relative to one another and forming a channel therebetween;
wherein one of said outer and inner components is connected to said rotary element and the other of said outer and inner components is connected to the smart device;
an amount of magnetorheological medium disposed in said channel for influencing the coupling intensity between said rotary element and the smart device;
a magnetic field generating unit configured for generating a magnetic field in said channel in order to influence a characteristic of said magnetorheological medium in said channel by way of the magnetic field;
wherein at least one property of the haptic interface changes depending on a currently selected menu and an intensity of the magnetic field generated by said magnetic field generating unit defines a haptic behavior of said haptic element and a resistance to the movement of said rotary element.

16. The haptic interface according to claim 15, wherein said magnetic field generating unit is configured to generate haptic feedback via variable detent torques with respect to a strength, a rotational angle, or an end stop for a rotation of said rotary element.

17. The haptic interface according to claim 15, wherein the haptic behavior is a resistance to a rotation of the rotary element in coordination with a currently selected menu item of the menu.

\* \* \* \* \*